United States Patent
Cleeves et al.

(10) Patent No.: US 10,413,585 B2
(45) Date of Patent: Sep. 17, 2019

(54) LIPOPEPTIDES FOR USE IN TREATING LIVER DISEASES AND CARDIOVASCULAR DISEASES

(71) Applicants: RUPRECHT-KARLS-UNIVERSITAET HEIDELBERG, Heidelberg (DE); Volker Cleeves, Weingarten (DE)

(72) Inventors: Volker Cleeves, Weingarten (DE); Stephan Urban, Neustadt/Weinstrasse (DE); Ralf Kubitz, Duesseldorf (DE)

(73) Assignee: RUPRECHT-KARLS-UNIVERSITÄT HEIDELBERG, Heidelberg (DE)

( * ) Notice: Subject to any disclaimer, the term of this patent is extended or adjusted under 35 U.S.C. 154(b) by 0 days.

(21) Appl. No.: 14/442,304

(22) PCT Filed: Nov. 12, 2013

(86) PCT No.: PCT/EP2013/073600
§ 371 (c)(1),
(2) Date: May 12, 2015

(87) PCT Pub. No.: WO2014/072524
PCT Pub. Date: May 15, 2014

(65) Prior Publication Data
US 2016/0015775 A1    Jan. 21, 2016

Related U.S. Application Data

(60) Provisional application No. 61/859,476, filed on Jul. 29, 2013, provisional application No. 61/725,144, filed on Nov. 12, 2012.

(51) Int. Cl.
| | | |
|---|---|---|
| *A61K 38/16* | (2006.01) |
| *C07K 14/705* | (2006.01) |
| *A61K 38/17* | (2006.01) |
| *G01N 33/50* | (2006.01) |
| *G01N 33/68* | (2006.01) |
| *A61K 31/00* | (2006.01) |
| *A61K 31/575* | (2006.01) |
| *G01N 33/92* | (2006.01) |
| *C07K 14/005* | (2006.01) |
| *C12N 7/00* | (2006.01) |

(52) U.S. Cl.
CPC ............ *A61K 38/162* (2013.01); *A61K 31/00* (2013.01); *A61K 31/575* (2013.01); *A61K 38/1709* (2013.01); *C07K 14/005* (2013.01); *C07K 14/705* (2013.01); *C12N 7/00* (2013.01); *G01N 33/5023* (2013.01); *G01N 33/5067* (2013.01); *G01N 33/6893* (2013.01); *G01N 33/92* (2013.01); *C12N 2730/10122* (2013.01); *C12N 2730/10132* (2013.01); *G01N 2333/705* (2013.01); *G01N 2500/04* (2013.01); *G01N 2500/10* (2013.01); *G01N 2800/085* (2013.01)

(58) Field of Classification Search
CPC .... A61K 38/162; A61K 31/00; A61K 31/575; A61K 38/1709; C07K 14/005; C07K 14/705; C12N 7/00; C12N 2730/10122; C12N 2730/10132; C12N 33/6893; C12N 33/92; G01N 33/5023; G01N 33/5067; G01N 2500/04; G01N 2333/705; G01N 2500/10; G01N 2800/085; G01N 33/92; G01N 33/6893

See application file for complete search history.

(56) References Cited

FOREIGN PATENT DOCUMENTS

| CN | 101970464 A | 2/2011 | |
|---|---|---|---|
| CN | 104662036 A | 5/2015 | |
| WO | WO /2009/092611 | * 7/2009 | ............ C07K 14/02 |

OTHER PUBLICATIONS

Cressman et al., Lipoprotein(a) Is an Independent Risk Factor for Cardiovascular Disease in Hemodialysis Patients, Circulation, vol. 86, no. 2 Aug. 1992, pp. 475-482.*
Arrebola et al., Iturin A is the principal inhibitor in the biocontrol activity of Bacillus amyloliquefaciens PPCB004 against postharvest fungal pathogens, Jl. Applied Micro, 108 (2010) 386-395.*
Kim et al., Modulation of Drugs of Human Hepatic Sodium-Dependent Bile Acid Transporter Activity, Jl. of Pharm. and Exp. Ther. 1204-1209, 1999 (supplied in IDS).*

(Continued)

*Primary Examiner* — Sudhakar Katakam
(74) *Attorney, Agent, or Firm* — Saliwanchik, Lloyd & Eisenschenk

(57) ABSTRACT

The present invention relates to lipopeptide-based compounds for use in the diagnosis, prevention and/or treatment of a liver disease or condition, preferably liver involved metabolic diseases, as well as in the control or modification of the cholesterol level or cholesterol uptake and, thus, diagnosis, prevention and/or treatment of a cardiovascular disease. The present invention furthermore relates to an in vitro or in vivo assay or method for testing or measuring the NTCP-mediated transport of test compound(s). The present invention furthermore relates to a method for the diagnosis, prevention and/or treatment of a liver disease or condition, comprising administering a therapeutically effective amount of a lipopeptide-based compound to a patient. The present invention furthermore relates to a method for the diagnosis, prevention and/or treatment of a cardiovascular disease.

19 Claims, 6 Drawing Sheets

Specification includes a Sequence Listing.

(56) References Cited

OTHER PUBLICATIONS

Schulze et al., Abstract of Preclinical studies on Myrcludex B, a novel Hepatitis B virus (HBV)-envelope protein derived entry inhibitor, Z Gastroenterol 2010; 48—P4_43.*

Dong et al. Structure Activity Relationship for FDA Approved Drugs as Inhibitors of the Human Sodium Taurocholate Co-transporting Polypeptide (NTCP), Mol Pharm. Mar. 4, 2013; 10(3): 1008-1019.*

John Y. L. Chiang, Bile acids: regulation and synthesis, Jl. of Lipid Res., vo. 50, 1955-1966, 2009.*

Huan, Yan et al., "Sodium Taurocholate Cotransporting Polypeptide is a functional receptor for hepatitis B and D virus," *Elife*, 2012, 1-28.

Kim, Richard et al., "Modulation by drugs of human hepatic sodium-dependent bile acid transporter (sodium taurocholate contransporting polypeptide) activity," *Journal of Pharmacology and Experimental Therapeutics*, 1999, 291(3):1204-1209.

Luetgehetmann, Marc et al., "Humanized chimeric uPA mouse model for the study of hepatitis B and D virus interactions and preclinical drug evaluation," *Hepatology*, 2012, 55(3):685-694.

Petersen, Joerg et al., "Prevention of hepatitis B virus infection in vivo by entry inhibitors derived from the large envelope protein," *Nature Biotechnology*, 2008, 26(3):335-341.

Zhong et al., "Sodium Taurocholate Contrasporting Polypeptide Mediates Woolly Monkey Hepatitis B Virus Infection—of Tupaia Hepatocytes," Journal of Virology, Jun. 2013, pp. 7176-7184, vol. 87, No. 12.

\* cited by examiner

Figure 1 A, B
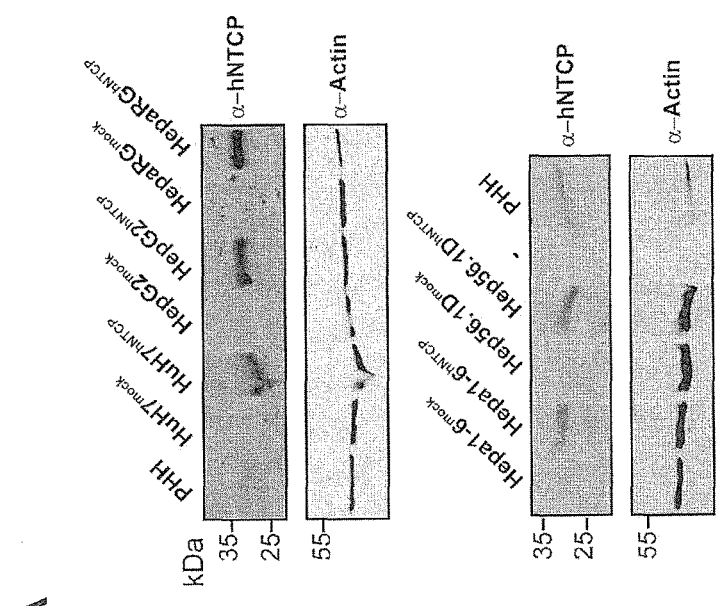

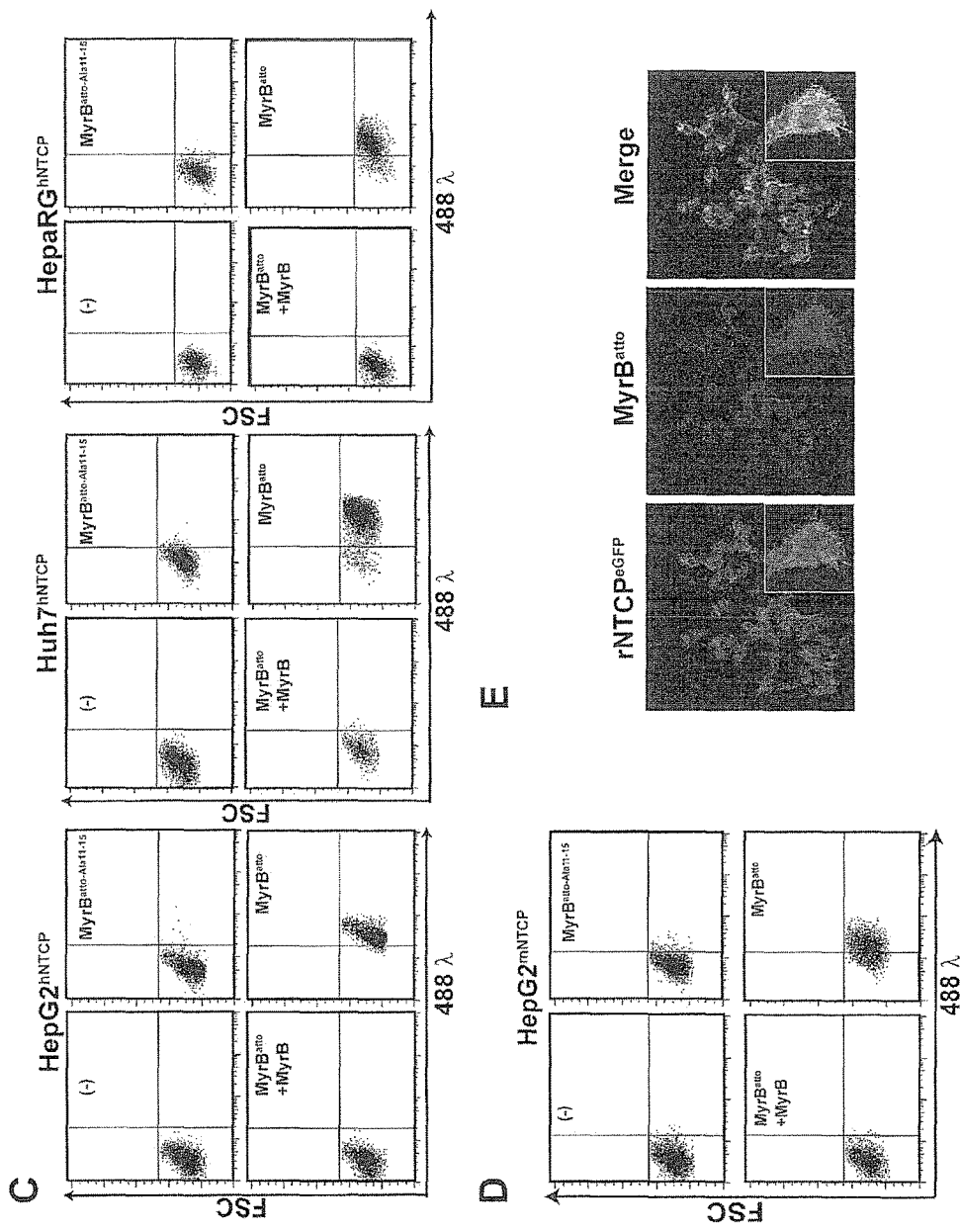

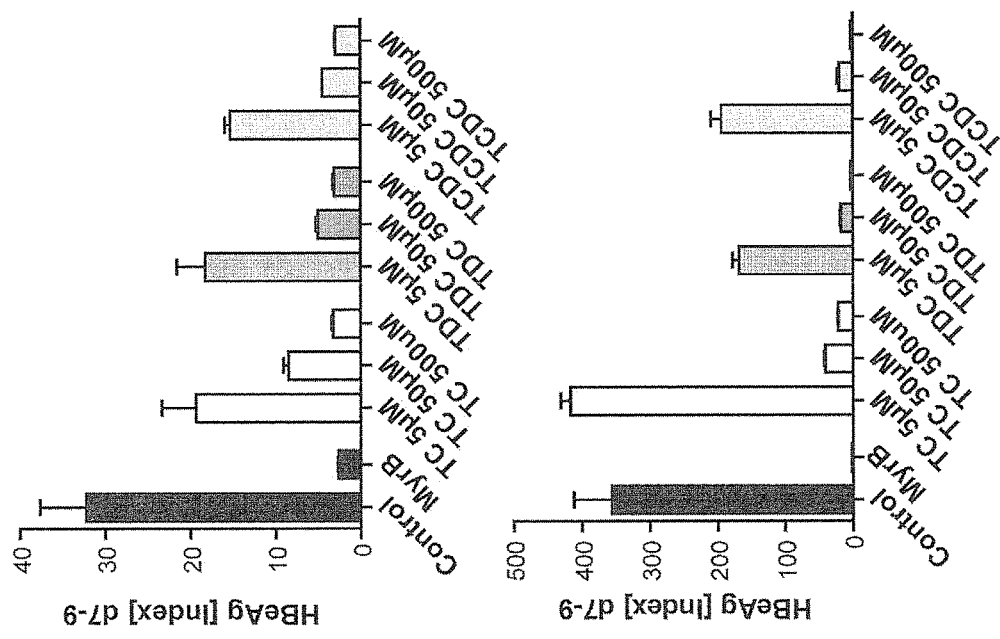
Figure 2 C, D

LIPOPEPTIDES FOR USE IN TREATING LIVER DISEASES AND CARDIOVASCULAR DISEASES

CROSS REFERENCE TO A RELATED APPLICATION

This application is a National Stage Application of International Application Number PCT/EP2013/073600, filed Nov. 12, 2013; which claims the benefit of U.S. Provisional Patent Applications Ser. No. 61/725,144, filed Nov. 12, 2012 and Ser. No. 61/859,476, filed Jul. 29, 2013; all of which are incorporated herein by reference in their entirety.

The Sequence Listing for this application is labeled "SEQ-LIST15Apr15.TXT", which was created on Apr. 15, 2015, and is 8 KB. The entire content is incorporated herein by reference in its entirety.

The present invention relates to lipopeptide-based compounds for use in the diagnosis, prevention and/or treatment of a liver disease or condition, preferably liver involved metabolic diseases, as well as in the control or modification of the cholesterol level or cholesterol uptake and, thus, diagnosis, prevention and/or treatment of a cardiovascular disease. The present invention furthermore relates to an in vitro or in vivo assay or method for testing or measuring the NTCP-mediated transport of test compound(s). The present invention furthermore relates to a method for the diagnosis, prevention and/or treatment of a liver disease or condition, comprising administering a therapeutically effective amount of a lipopeptide-based compound to a patient. The present invention furthermore relates to a method for the diagnosis, prevention and/or treatment of a cardiovascular disease.

BACKGROUND OF THE INVENTION

The human hepatitis B virus (HBV) is a member of the hepadnaviridae. Hepadnaviruses are the smallest enveloped DNA viruses which replicate via reverse transcription of a pgRNA intermediate. During assembly the nucleocapsid acquires three viral envelope proteins termed large (L), middle (M) and small (S). They are encoded in one open reading frame and share the S-domain which is required for membrane anchoring. In addition to the S-domain, M contains an N-terminal hydrophilic extension of 55 amino acids (preS2), while L is further extended by 107, 117 or 118 amino acids (genotype-dependent) termed preS1 (Urban 2008). The hepatitis D virus (HDV) is a satellite virusoid utilizing the HBV envelope proteins for entry into hepatocytes. The myristoylated preS1-domain of L is known to play the key role in HBV and HDV infectivity.

The inventors have previously identified HBV L-protein derived lipopeptides that block HBV and HDV infection of PHH and HepaRG cells (Gripon et al., 2005, Schulze et al., 2010, WO 2009/092611 A1). They represent the N-terminal 47 amino acids of the preS1-domain of HBV (HBVpreS/2-48$^{myr}$) and include the naturally occurring modification with myristic acid.

In WO 2009/092612 and WO 2012/107579, whose contents are incorporated herewith by reference in its entirety, the inventors describe hydrophobic modified preS-derived peptides of HBV and their use as vehicles for the specific delivery of compounds to the liver.

The inventors have furthermore previously identified the receptor responsible for the binding of these HBV L-protein derived lipopeptides, namely sodium taurocholate co-transporting polypeptide (NTCP/SLC10A1). (U.S. Provisional application 61/725,144, filed Nov. 12, 2012). NTCP is an integral transmembrane protein, not expressed in HepG2, HuH7, induced in HepaRG cells after DMSO treatment (Kotani et al., 2012) and down-modulated in primary hepatocytes during de-differentiation (Doring et al., 2012).

In particular, the inventors have identified a novel HBV preS1-specific receptor playing a key role in Hepatitis B virus (HBV) and/or Hepatitis D virus (HDV) infection, the human sodium taurocholate cotransporter polypeptide NTCP/SLC10A1. Expression of this receptor or of certain non-human counterparts allows to transform cells that were previously unable to bind HBV and/or HDV and/or non-susceptible to HBV and/or HDV infection into cells that are HBV and/or HDV binding-competent and/or susceptible to HBV and/or HDV infection. Cells that are already susceptible to HBV and/or HDV infection (HepaRG cells) show a significantly increased susceptibility upon expression of NTCP.

Also Yan et al. (2012) identified NTCP/SLC10A1 as a preS-specific receptor in primary Tupaia hepatocytes (PTH) and demonstrate that human (h) NTCP promotes HBV/HDV entry into hepatoma cells.

The liver plays a predominant role in drug biotransformation and disposition from the body. In view of its barrier function between the gastrointestinal tract and systemic blood, it is constantly exposed to ingested xenobiotics entering the portal circulation. Drug-induced liver injury accounts for up to 7% of all reports of adverse drug effects voluntarily reported to pharmacovigilance registries. Drugs cause direct damage to hepatocytes, bile ducts or vascular structures or may interfere with bile flow. The phenotypes commonly encountered thus include hepatitis, cholestasis, steatosis, cirrhosis, vascular and neoplastic lesions and even fulminant hepatic failure. Almost every drug has the potential to cause hepatic injury, be it through direct toxicity of the agent or through an idiosyncratic response of the individual. The susceptibility of the liver to injury by drugs is influenced by various factors such as age, sex, pregnancy, comedication, renal function and genetic factors (Kullak-Ublick, 2000).

Drug induced cholestatic liver disease is a subtype of liver injury that is characterized by predominant elevations of alkaline phosphatase and bilirubin secondary to the administration of a hepatotoxic agent. It can manifest itself as a cholestatic hepatitis or as bland cholestasis, depending upon the causative agent and the mechanism of injury. Drugs that typically cause cholestasis with hepatitis include psychotropic agents, antibiotics and nonsteroidal antiinflammatory drugs (NSAIDs). The mechanism is immunoallergic and results from hypersensitivity. Pure cholestasis without hepatitis is observed most frequently with contraceptive and 17α-alkylated androgenic steroids and the mechanism most likely involves interference with hepatocyte canalicular efflux systems for bile salts, organic anions and phospholipids. The rate-limiting step in bile formation is considered to be the bile salt export pump (BSEP) mediated translocation of bile salts across the canalicular hepatocyte membrane. Inhibition of BSEP function by metabolites of cyclosporine A, troglitazone, bosentan, rifampicin and sex steroids is an important cause of drug induced cholestasis (Kullak-Ublick, 2000).

There is a need in the art for improved means and methods for treating liver involved metabolic diseases, drug induced toxicity and cholestatic liver diseases, as well as cardiovascular diseases.

SUMMARY OF THE INVENTION

According to the present invention this object is solved by providing a lipopeptide-based compound for use in the diagnosis, prevention and/or treatment of a liver disease or condition, wherein said liver disease or condition is related to sodium taurocholate cotransporter polypeptide (NTCP)-mediated transport of compounds into hepatocytes.

According to the present invention this object is solved by providing a lipopeptide-based compound for use in the diagnosis, prevention and/or treatment of a cardiovascular disease.

According to the present invention this object is solved by an in vitro or in vivo assay or method for testing or measuring the NTCP-mediated transport of test compound (s), comprising the steps of
(a) providing test compound(s) and a lipopeptide-based compound as defined in the present invention;
(b) providing a test system for functional and selective NTCP expression;
(c) adding the test compound(s), either together with or without the lipopeptide-based compound, to the NTCP test system of (b);
(d) determining whether the test compound(s) are transported via NTCP by comparing the results of step (b) and (c) each with or without the addition of the lipopeptide-based compound,
wherein a test compound is considered being transported via NTCP when the compound(s) decrease, block or inhibit bile salt transport by NTCP (competitive transport) or when the transport of the compound(s) can be decreased, blocked or inhibited by the addition of the lipopeptide-based compound.

According to the present invention this object is solved by a method for the diagnosis, prevention and/or treatment of a liver disease or condition,
wherein said liver disease or condition is related to sodium taurocholate cotransporter polypeptide (NTCP)-mediated transport of compounds into hepatocytes,
comprising administering a therapeutically effective amount of a lipopeptide-based compound to a patient.

According to the present invention this object is solved by a method for the diagnosis, prevention and/or treatment of a cardiovascular disease.

According to the present invention this object is solved by a method for the control or modification of the cholesterol level or cholesterol uptake, comprising administering a therapeutically effective amount of a lipopeptide-based compound to a patient.

DESCRIPTION OF THE PREFERRED
EMBODIMENTS OF THE INVENTION

Before the present invention is described in more detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art. For the purpose of the present invention, all references cited herein are incorporated by reference in their entireties.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "at least 4 amino acids, preferably 4 to 19" should be interpreted to include not only the explicitly recited values of 4 to 19, but also include individual values and sub-ranges within the indicated range. Thus, included in this numerical range are individual values such as 4, 5, 6, 7, 8, 9, 10, 11, 12, 13, 14, 15, 16, 17, 18, 19, and sub-ranges such as from 4 to 10, from 6 to 15, from 10 to 19, from 8 to 19 and from 15 to 19, etc. As an illustration, a numerical range of "at least 1 amino acid, preferably 1 to 78" should be interpreted to include not only the explicitly recited values of 1 to 78, but also include individual values and sub-ranges within the indicated range. Thus, included in this numerical range are individual values such as 1, 2, 3, 4, 5, 6, 7, 8, 9, 10 . . . 75, 76, 77, 78, and sub-ranges such as from 10 to 50, from 15 to 40, from 8 to 35, from 30 to 50, and from 20 to 40, etc. This same principle applies to ranges reciting only one numerical value. Furthermore, such an interpretation should apply regardless of the breadth of the range or the characteristics being described.

Use of Lipopeptides in the Treatment of Liver Diseases

As discussed above, the present invention provides a lipopeptide-based compound for use in the diagnosis, prevention and/or treatment of a liver disease or condition.

Said liver disease or condition is related to sodium taurocholate cotransporter polypeptide (NTCP)-mediated transport of compounds into hepatocytes.

Preferably, said liver disease or condition that is related to NTCP-mediated transport of compounds into hepatocytes, is a liver involved metabolic disease selected from
intrahepatic cholestasis,
poisoning of the liver (by liver toxins)/hepatotoxicity,
drug-induced cholestatic liver disease,
hyperlipidemia.

Lipopeptide-based Compound

The lipopeptide-based compound preferably comprises:
(a) a peptide or amino acid sequence,
(b) a hydrophobic or lipid-modification, preferably at the peptide (a),
(c) optionally, a further moiety or further moieties.

Preferably, the peptide or amino acid sequence (a) has or comprises the general formula

X-P-Y wherein
P is the amino acid sequence NPLGFXaaP SEQ. ID NO: 1,
(single letter amino acid code)
wherein Xaa is an arbitrary amino acid; preferably F or L, more preferably F
(thus, P is preferably NPLGFFP or NPLGFLP) (amino acid positions 20-26 of SEQ ID NO:2) or NPLGFLP) (amino acid positions 8-14 of SEQ ID NO:21);
X is an amino acid sequence having a length of m amino acids,
wherein m is at least 4;
Y is an amino sequence having a length of n amino acids,
wherein n is 0 or at least 1;
and wherein m+n≥11.

The peptide or amino acid sequence (a) (having the general formula X-P-Y) is preferably derived from the preS domain of hepatitis B virus (HBV) (also designated "preS-peptide"). The envelope of HBV encloses three proteins termed L (large), M (middle) and S (small). They share the C-terminal S-domain with four transmembrane regions. The M- and L-protein carry additional N-terminal extensions of 55 and, genotype-dependent, 107 or 118 amino acids (preS2- and preS1).

A peptide or amino acid sequence (a) preferably refers to a peptide with an amino acid sequence that corresponds to or is based on the N-terminal extensions of the L-protein of HBV, preS1, preferably of genotypes A to H as well as of woolly monkey (WMHBV), orangutan, chimpanzee and gorilla hepatitis B viruses, but it also refers to variants thereof, preferably C-terminally truncated variants, amino acid substitution variants.

As an indispensible or essential sequence, the amino acid residues being important for the binding of the lipopeptide-based compounds of the present invention to NTCP, as set out in SEQ ID NO: 1 (NPLGFXaaP) are present in the peptide/amino acid sequence (a) of the lipopeptide-based compounds of the invention.

In particular, the peptides are based on the following sequences (amino acids in single letter code; essential domain underlined).

```
Essential domain (SEQ ID NO: 1):
NPLGFXP (wherein X or Xaa is an arbitrary amino
acid, preferably F or L, more preferably F)

preS HBV-A (ID: M57663; SEQ ID NO: 2):
MGGWSSKPRKGMGTNLSVPNPLGFFPDHQLDPAFGANSNNPDWDFNPIKD

HWPQANQVGVGAFGPGFTPPHGGVLGWSPQAQGILATVPAMPPPASTNRQ

SGRQPTPISPPLRDSHPQA preS HBV-B (ID: D00329, SEQ ID NO: 3)
MGGWSSKPRKGMGTNLSVPNPLGFFPDHQLDPAFKANSENPDWDLNPHKD

NWPDAHKVGVGAFGPGFTPPHGGLLGWSPQAQGILTSVPAAPPPASTNRQ

SGRQPTPLSPPLRDTHPQA preS HBV-C (ID: AB048704, SEQ ID NO: 4)
MGGWSSKPRKGMGTNLSVPNPLGFFPDHQLDPAFKANSENPDWDLNPHKD

NWPDAHKVGVGAFGPGFTPPHGGLLGWSPQAQGILTSVPAAPPPASTNRQ

SGRQPTPLSPPLRDTHPQA preS HBV-Chimpanzee (ID: AB032432, SEQ ID NO: 5)
MGQNLSTSNPLGFFPEHQLDPAFKANTNNPDWDFNPKKDYWPEANKVGAG

AFGPGFTPPHGGLLGWSPQAQGILTTLPANPPPASTNRQSGRQPTPLSPP

LRDTHPQA preS HBV-D (ID: AB048702, SEQ ID NO: 6)
MGQNLSTSNPLGFFPDHQLDPAFRANTNNPDWDFNPNKDTWPDANKVGAG

AFGLGFTPPHGGLLGWSPQAQGFQTLPANPPPASTNRQSGRQPTPLSPPL

RTTHPQA preS HBV-E (ID: X65657, SEQ ID NO: 7)
MGLSWTVPLEWGKNISTTNPLGFFPDHQLDPAFRANTRNPDWDHNPNKDH

WTEANKVGVGAFGPGFTPPHGGLLGWSPQAQGMLKTLPADPPPASTNRQS

GRQPTPITPPLRDTHPQA preS HBV-F (ID: X69798@8, SEQ ID NO: 8)
MGAPLSTTRRGMGQNLSVPNPLGFFPDHQLDPLFRANSSSPDWDFNTNKD

SWPMANKVGVGGYGPGFTPPHGGLLGWSPQAQGVLTTLPADPPPASTNRR

SGRKPTPVSPPLRDTHPQA preS HBV-G (ID: AF160501, SEQ ID NO: 9)
MGLSWTVPLEWGKNLSASNPLGFLPDHQLDPAFRANTNNPDWDFNPKKDP

WPEANKVGVGAYGPGFTPPHGGLLGWSPQSQGTLTTLPADPPPASTNRQS

GRQPTPISPPLRDSHPQA

HBV Gibbon (ID: AJ131572, SEQ ID NO: 10)
MGQNHSVTNPLGFFPDHQLDPLFRANSNNPDWDFNPNKDTWPEATKVGVG

AFGPGFTPPHGGLLGWSPQAQGILTTLPAAPPPASTNRQSGRKATPISPP

LRDTHPQA

HBV-H (ID: Q8JMY6, SEQ ID NO: 11)
MGAPLSTARRGMGQNLSVPNPLGFFPDHQLDPLFRANSSSPDWDFNTNKD

NWPMANKVGVGGFGPGFTPPHGGLLGWSPQAQGILTTSPPDPPPASTNRR

SGRKPTPVSPPLRDTHPQA

HBV Orangutan (ID: AF 193864, SEQ ID NO: 12)
MGQNLSVSNPLGFFPEHQLDPLFRANTNNPDWDFNPNKDTWPEATKVGVG

AFGPGFTPPHGGLLGWSPQAQGVTTILPAVPPPASTNRQSGRQPTPISPP

LRDTHPQA

HBV Woolly Monkey (ID: NC 001896, SEQ ID NO: 13)
MGLNQSTFPLGFFPSHQLDPLFKANAGSADWDKPKDPWPQAHDTAVGAFG

PGLVPPHGGLLGWSSQAQGLSVTVPDTPPPPSTNRDKGRKPTPATPPLRD

THPQA
```

There also exists a HBV preS consensus sequence (for amino acid positions (−11) to 48) (SEQ ID NO: 14):

```
(-11)-M GGWSS TPRKG MGTNL SVPNP LGFFP DHQLD PAFRA

NSNNP DWDFN PNKDH WPEAN KVG-48
```

"Variants" are preferably N-terminally and/or C-terminally truncated variants, amino acid substitution or deletion variants, or prolonged variants of the sequences of SEQ ID NOs: 2-14, carrying a hydrophobic modification and wherein, optionally, one or more further moiety or moieties is/are coupled to one or amino acid(s) N- or C-terminal of the essential domain. Variants comprise furthermore an amino acid sequence comprising modified amino acid(s), unnatural amino acid(s) or peptidomimetic(s) or further compounds which can mimic a peptide backbone/structure. Preferably, variants are selected from C-terminally truncated variants of SEQ ID NOs. 2 to 14; amino acid substitution or deletion variants; variants comprising modified amino acid (s), unnatural amino acid(s) or peptidomimetic(s) or further compounds which can mimic a peptide backbone/structure.

Furthermore, the peptide or amino acid sequences are preferably L-amino acid sequences, but can also comprise D-amino acids or are D-amino acid sequences.

According to the invention, the peptide of the lipopeptide-based compound comprises at least the amino acids having the sequence of SEQ ID NO: 1 and can consist of 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118 or 119 amino acids of the above SEQ ID NOs: 2 to 14, or variants thereof.

N-terminally and/or C-terminally truncated variants comprise preferably at least 18 consecutive amino acids, more preferably at least 19 consecutive amino acids, even more preferably at least 20 and just even more preferably at least 21 consecutive amino acids of SEQ ID NOs. 2 to 14 or variants thereof.

The N-terminal sequence X of the peptide having a length of m amino acids comprises at least 4 amino acids (i.e. m is at least 4). Preferably, the N-terminal sequence X can consist of 4, 5, 6, 7, 8, 9, 10, 11, 12, 13, 14, 15, 16, 17, 18, or 19 amino acids. That is, m may be 4 to 19.

In one embodiment, one or amino acid(s) of X have an amino group in a side chain, which is/are preferably selected from lysine, α-amino glycine, α,γ-diaminobutyric acid, ornithine, α,β-diaminopropionic acid, more preferably lysine. The amino acid(s) of X having an amino group in a side chain, is/are preferably is/are located at the N-terminus of X, wherein one to eleven (1-11), preferably one to three (1-3), amino acids having an amino group in a side chain are located at the N-terminus of X.

In one embodiment, the N-terminal sequence X preferably comprises the sequence $NX_1SX_2X_3$ (SEQ ID NO: 15), wherein $X_1$, $X_2$ and, $X_3$ may be arbitrary amino acids. Preferably, $X_1$ of SEQ ID NO: 15 is L, I or Q, more preferably L. Preferably, $X_2$ of SEQ ID NO: 15 is T, V, A or is not present, preferably T or V, more preferably T. Preferably, $X_3$ of SEQ ID NO: 15 is P, S, T or F, more preferably P or S, even more preferably S. Preferably, the sequence $NX_1SX_2X_3$ (SEQ ID NO: 15) is directly attached to the N-terminus of the amino acid sequence P (SEQ. ID NO: 1; NPLGFXaaP), resulting in a peptide comprising the sequence $NX_1SX_2X_3NPLGFXaaP$, wherein $X_1$, $X_2$, $X_3$ and Xaa are defined as above.

The C-terminal sequence Y of the peptide having a length of n amino acids comprises 0 or at least 1 amino acids (i.e. n=0 or n is at least 1). Preferably, the C-terminal sequence Y can consist of 0, 1, 2, 3, 4, 5, 6, 7, 8, 9, 10, 11, 12, 13, 14, 15, 16, 17, 18, 19 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 78, 79, 80, 81, 82, 83, 84, 85, 86, 87, 88, 89, 90, 91, 92 or 93 amino acids. That is, n may be 0 to 93.

In one embodiment, the C-terminal sequence Y consists of at least 4 amino acids (i.e. n is at least 4), which preferably has the sequence $X_4HQLDP$ (SEQ ID NO: 16), wherein $X_4$ is an arbitrary amino acid. Preferably, $X_4$ of SEQ ID NO: 16 is D, E or S, more preferably D or E, even more preferably D. Preferably, the sequence $X_4HQLDP$ (SEQ ID NO: 16) is directly attached to the C-terminus of the amino acid sequence P (SEQ. ID NO: 1; NPLGFXaaP), resulting in a peptide comprising the sequence $NPLGFXaaPX_4HQLDP$, wherein $X_4$ and Xaa are defined as above.

In a preferred embodiment, the peptide of the lipopeptide-based compound of the present invention comprises a peptide encoded by the amino acid sequence $NX_1SX_2X_3NPLGFXaaP$ $X_4HQLDP$ (SEQ ID NO: 17), wherein $X_1$, $X_2$, $X_3$, $X_4$ and Xaa are defined as above.

The term "variant" also refers to the homologous sequences found in the different viral species, strains or subtypes of the hepadnavirus genus, such as HBV strain alpha, HBV strain LSH (chimpanzee isolate), woolly monkey HBV (WMHBV), or strains selected from the group consisting of the HBV genotypes A to H (see SEQ ID NO: 2-13).

The term "variant" also refers to homologous sequences which show at least 50% sequence identity to an amino acid sequence comprising the invariant NPLGFXaaP-domain and the adjacent sequences of SEQ ID NO. 2-14 or any other amino acid sequence disclosed herein, preferably 70%, more preferably 80%, even more preferably 90% or 95%.

Thus, a preferred peptide/amino acid sequence (a) according to the invention comprises a variant of SEQ ID NOs. 2 to 14 with an amino acid sequence of the different viral species, strains or subtypes, preferably of the genotypes of HBV or woolly monkey HBV (WMHBV) or variants thereof.

"Variants" of SEQ ID NOS. 2 to 14 also comprise variants or "analogues" comprising amino acid deletions, amino acid substitutions, such as conservative or non-conservative replacement by other amino acids or by isosteres (modified amino acids that bear close structural and spatial similarity to protein amino acids), amino acid additions or isostere additions, as long as the sequence still binds to NTCP.

Conservative amino acid substitutions typically relate to substitutions among amino acids of the same class. These classes include, for example,
  amino acids having uncharged polar side chains, such as asparagine, glutamine, serine, threonine and tyrosine;
  amino acids having basic side chains, such as lysine, arginine, and histidine;
  amino acids having acidic side chains, such as aspartic acid and glutamic acid; and
  amino acids having nonpolar side chains, such as glycine, alanine, valine, leucine, isoleucine, proline, phenylalanine, methionine, tryptophan, and cysteine.

As discussed above, the peptide or amino acid sequences (a) are preferably L-amino acid sequences, but can also comprise D-amino acids or are D-amino acid sequences.

Preferably, the peptide or amino acid sequence (a), X-P-Y is selected from a peptide comprising an amino acid sequence selected from

| | |
|---|---|
| SEQ ID NO. 18 | HBV preS/2-48 (genotype C), |
| SEQ ID NO. 19 | HBV preS/2-48 (genotype D), |
| SEQ ID NO. 20 | HBV preS/2-48 (consensus), or | an amino acid sequence having at least 90% sequence identity (preferably at least 95% or 99% identity) to the above sequences
and variants thereof.

In this embodiment, m=7 and n=33 (m+n=40), resulting in a peptide or amino acid sequence of 47 amino acids.

```
SEQ ID NO. 18
GTNL SVPNP LGFFP DHQLD PAFGA NSNNP DWDFN PNKDH

WPEAN KVG

SEQ ID NO. 19
GQNL STSNP LGFFP DHQLD PAFRA NTANP DWDFN PNKDT

WPDAN KVG

SEQ ID NO. 20:
GTNL SVPNP LGFFP DHQLD PAFRA NSNNP DWDFN PNKDH

WPEAN KVG
```

In a preferred embodiment, the lipopeptide is Myrcludex B:
(a) having the amino acid sequence of HBV preS/2-48 (genotype C) with SEQ ID NO. 18.

The lipopeptide-based compound according to the invention preferably comprises:
(b) a hydrophobic or lipid-modification, preferably at the peptide (a).

Preferably, the peptide comprises a hydrophobic or lipid-modification (b), such as at the N-terminus, the C-terminus or at an amino acid side chain.

In one embodiment, the peptide is modified with at least one hydrophobic moiety or group. In preferred embodiments of this invention, the peptide is modified with 1, 2, 3, 4 or more hydrophobic moiety/ies or group(s). That is, the peptide can be modified with more than one hydrophobic moiety or group, such as 2. The hydrophobic moieties or groups can be the same or different to each other.

The hydrophobic modification is preferably selected from: acylation and/or addition of hydrophobic moieties.

Preferably, the peptide comprises an N or C-terminal hydrophobic modification (b).

An N-terminal hydrophobic modification is preferred.

"N-terminal" refers to the N-terminus of a peptide, thus in a peptide with the general formula X-P-Y, it refers to the N-terminus of X, i.e. the respective first amino acid residue, but comprises also the hydrophobic modification in close proximity to the N-terminus, such as respective amino acid residues (−4), (−3), (−2), (−1), 1, 2 or 3 or 4. Thus, the coupling of the hydrophobic modification can furthermore be obtained by an attachment of a hydrophobic moiety at a site close to the N-terminus of X.

The hydrophobic modification of the lipopeptide-based compound according to the present invention adds a hydrophobic moiety, preferably to the peptide/amino acid sequence.

Acylation is preferably selected from acylation with carboxylic acids, fatty acids, amino acids with lipophilic side chains. Preferred fatty acids are saturated or unsaturated fatty acids, branched or unbranched fatty acids, preferably with 8 to 22 carbon atoms (C 8 to C 22). More preferably, the hydrophobic modification by acylation is selected from acylation with myristoyl (C 14), palmitoyl (C 16) or stearoyl (C 18). Modification by myristoylation is preferred in in vivo and medicinal applications due to its higher safety, e.g. not showing the adverse effects of the stearoyl group (innate immune response etc).

The addition of hydrophobic moieties is preferably selected from addition of cholesterol, derivatives of cholesterol, phospholipids, glycolipids, glycerol esters, steroids, ceramids, isoprene derivatives, adamantane, farnesol, aliphatic groups, polyaromatic compounds, oleic acid, bile salts or bile salt conjugates, more preferably oleic acid, cholesterol, bile salts or bile salt conjugates. The attachment of the hydrophobic moieties is preferably by covalent binding, which can be achieved via carbamate, amide, ether, disulfide or any other linkage that is within the skill of the person skilled in the art.

Thus, the peptide/amino acid sequences (a) are preferably hydrophobically modified, preferably acylated and, thus, preferably lipopeptides due to their lipophilic or hydrophobic group/moiety.

In one embodiment, the peptide or amino acid sequence (a) has or comprises the general formula X-P-Y-R$_o$ wherein P, X, and Y are as defined above and
R is a C-terminal modification of said hydrophobic modified peptide,
which is preferably a moiety that protects from degradation selected from amide, D-amino acid, modified amino acid, cyclic amino acid, albumin, natural and synthetic polymer, such as PEG, glycane,
o is 0 or at least 1.

The C-terminal modification (R) of Y is preferably a modification with a moiety that protects from degradation, such as in vivo degradation.

"C-terminal" refers to the modification at the C-terminus, i.e. the respective last amino acid residue, but comprises also the modification in close proximity to the C-terminus, such as the last but one amino acid residue, the last but two amino acid residue or more amino acid residues (e.g. introduction of one D-amino acid that protects the carrier from enzymatic degradation e.g. by the action of carboxypeptidases). The skilled artisan will be able to select the respective suitable moiety(s) depending on the respective application. Preferred moieties that protect from degradation are selected from amides, D-amino acids, modified amino acids, cyclic amino acids, albumin, natural and synthetic polymers, such as PEG, glycane. Furthermore, o is 0 or at least 1, i.e. the C-terminal modification (R) is optional. Preferably, o is 1. In further embodiments of this invention o is 1, 2, 3, 4 or more. That is, the C-terminus or its proximity can be modified with more than one moiety or group, such as 2. The moieties or groups can be the same or different to each other.

In one embodiment, the preferred C-terminal modification is an amide.

In an embodiment of this invention the hydrophobic modification and/or R are linked to the peptide via a linker or spacer. Linker or spacer are known to the skilled artisan, such as polyalanine, polyglycin, carbohydrates, (CHa)n groups. The skilled artisan will, thus, be able to select the respective suitable linker(s) or spacer(s) depending on the respective application.

In a preferred embodiment, the lipopeptide is Myrcludex B having
(a) the amino acid sequence of HBV preS/2-48 (genotype C) with SEQ ID NO. 18;
(b) an N-terminal myristoylation
(c) a C-terminal amide.

Myr-GTNLSVP<u>NPLGFFP</u>DHQLDPAFGANS<u>N</u>NPDWDFNPNKDHWPEANKV

-amide

In one embodiment, the lipopeptide-based compound according to the invention comprises
(c) a further moiety or moieties.
Such further moieties can be
drug(s) or their respective prodrug(s);
tag(s);
label(s), such as fluorescent dye(s), radioisotope(s) and contrast agent(s);
recombinant virus(s) or derivative(s) thereof;
carrier or depot(s) for drug(s), prodrug(s) or label(s);
immunogenic epitope(s);
hormones (peptide hormones, steroid hormones, monoamines, amino acid derivatives, eicosanoids).

In one embodiment, the further moiety or moieties are covalently attached to the lipopeptide-compound (preferably to the peptide), such as via linker, spacer and/or anchor group(s).

The lipopeptide-based compounds can further contain anchor group(s) that can serve as an additional point(s) of attachment for further moieties (such as compound, tag, label) and can be located at an amino acid of Y.

An anchor group can be at an amino acid side chain or can be the amino acid side chain itself, i.e. the anchor group can be a side chain itself or a modified side chain. The anchor group can also be a modified amino acid residue which was introduced into the amino acid sequence of the lipopeptide to serve as an anchor group. In other embodiments of the invention the anchor group A is attached to the hydrophobic modification and/or the C-terminal modification R.

Preferred anchor groups are selected from ester, ether, disulfide, amide, thiol, thioester. The skilled artisan will be able to select the respective suitable anchor group(s) depending on the respective further moiety to be attached. The anchor group can furthermore be suitable for attaching a complex-forming component, such as of the biotin/avidin, polyarginine/oligonucleotide (e.g. siRNA) complex. In some embodiments, there are more than one anchor group, such as 2, 3, 4 or more, such as 2. The anchor groups can be the same or different to each other, allowing the attachment of several further moieties.

In one embodiment, the further moiety/moieties is/are contrast agent(s) which are coupled via a chelating agent.

Thereby, the contrast agent is bound/coupled in the form of a complex with a chelating agent being able to form complexes with the respective contrast agent.

Such chelating agent can be 1,4,7, 10-tetraazacyclododecane-N,N',N,N'-tetraacetic acid (DOTA), ethylenediaminetetraacetic acid (EDTA), 1,4,7-triazacyclononane-1,4,7-triacetic acid (NOTA), triethylenetetramine (TETA), iminodiacetic acid, Diethylenetriamine-N,N,N', N',N''-pentaacetic acid (DTP A) and 6-Hydrazinopyridine-3-carboxylic acid (HYNIC), such as preferably DOTA.

Examples of contrast agents are paramagnetic agents, e.g. Gd, Eu, W and Mn, preferably complexed with a chelating agent. Further options are supramagnetic iron (Fe) complexes and particles, compounds containing atoms of high atomic number, i.e. iodine for computer tomography (CT), microbubbles (such as for contrast enhanced ultrasound (CEUS)) and carriers such as liposomes that contain these contrast agents.

The peptides of the invention can be prepared by a variety of procedures readily known to those skilled in the art, in general by synthetic chemical procedures and/or genetic engineering procedures. Synthetic chemical procedures include more particularly the solid phase sequential and block synthesis. More details can be taken from WO 2009/092612.

NTCP

Sodium/bile acid cotransporter also known as the sodium/Na⁺-taurocholate cotransporting polypeptide (NTCP) is a protein that in humans is encoded by the SLC10A1 (solute carrier family 10 member 1) gene.

Sodium/bile acid cotransporters are integral membrane glycoproteins that participate in the enterohepatic circulation of bile acids. Two homologous transporters are involved in the reabsorption of bile acids, one absorbing from the intestinal lumen, the bile duct, and the kidney with an apical localization (SLC10A2), and the other sodium-dependent cotransporter being found in the basolateral membranes of hepatocytes (SLC10A1).

Bile formation is an important function of the liver. Bile salts are a major constituent of bile and are secreted by hepatocytes into bile and delivered into the small intestine, where they assist in fat digestion. In the liver, hepatocytes take up bile salts (mainly via NTCP) and secrete them again into bile (mainly via the bile salt export pump (BSEP)) for ongoing enterohepatic circulation. Uptake of bile salts into hepatocytes occurs largely in a sodium-dependent manner by the sodium taurocholate cotransporting polypeptide NTCP. The transport properties of NTCP have been extensively characterized. It is an electrogenic member of the solute carrier family of transporters (SLC10A1) and transports predominantly bile salts and sulfated compounds, but is also able to mediate transport of additional substrates, such as thyroid hormones, drugs and toxins. It is highly regulated under physiologic and pathophysiologic conditions. Regulation of NTCP copes with changes of bile salt load to hepatocytes and prevents entry of cytotoxic amounts of bile salts during liver disease.

For a review of bile salt transporters, see also Trauner and Boyer (2003).

For NTCP a large range of substrates could be detected, it transports unconjugated as well as taurine-conjugated and glycine-conjugated bile acids (Hagenbuch & Meier, 1994), also sulfated bile acids and, in contrast to the apical sodium dependent bile acid transporter (ASBT), also steroid sulfates (Craddock et al 1998; Kramer et al, 1999; Schroeder et al 1998), and thyroid hormones (Friesema et al, 1999). Drugs like rosuvastatin (Ho et al., 2006) and micafungin (Yanni et al., 2010) have also been shown to have affinity for NTCP. Recent data show FDA-approved drugs that are identified as inhibitors of NTCP (Dong et al., 2013). Most of them are antifungal, antihyperlipidemic (simvastatin), antihypertensive, anti-inflammatory, or glucocorticoid drugs.

Preferably, the compounds which are transported into hepatocytes via NTCP are
  bile acids
    such as cholate
    taurine- or glycine conjugated bile acids and salts thereof
      (taurine- or glycine conjugated dihydroxy and trihydroxy bile salts)
      such as
      taurocholate
      glycocholate
      taurodeoxycholate
      taurochenodeoxycholate
      tauroursodeoxycholate
    sulfated bile acids and salts thereof
  steroides
    steroide sulfates
      estrogen conjugates (e.g. estrone-3-sulfate, 17α-ethinylestradiol-3-O-sulfate)
      dehydroepiandrosterone sulfate
  conjugated and non-conjugated thyroid hormones
  liver toxins
  compounds that are covalently bound to taurocholate (e.g. chlorambucil-taurocholate)
  bromosulphophthalein,
  drugs
    such as
    antifungal (e.g. micafungin),
    antihyperlipidemic (e.g. simvastatin, rosuvastatin, pitavastatin, fluvastatin,
    atorvastatin),
    antihypertensive,
    anti-inflammatory, or
    glucocorticoid drugs.

Preferably, said liver disease or condition that is related to NTCP-mediated transport of compounds into hepatocytes, is a liver involved metabolic disease selected from
  intrahepatic cholestasis,
  poisoning of the liver (by liver toxins)/hepatotoxicity,
  drug-induced cholestatic liver disease,
  hyperlipidemia,
  posthepatic cholestasis.

A "liver involved metabolic disease" when used herein refers to metabolic disorders including visceral obesity, diabetes mellitus and dyslipidemia which are influenced by the liver metabolism of lipids and bile acids.

In general, "cholestasis" is a condition where bile constituents cannot be secreted from hepatocytes into the biliary tree or where bile cannot flow from the liver to the duodenum, resulting in hepatocyte bile acid accumulation within hepatocytes.

"Cholestasis" or "intrahepatic cholestasis" when used herein refers to intrahepatic toxic effects of hepatocyte bile acid accumulation related to an insufficient expression and/or activity of bile salt pumps (like BSEP or MRP) in the canalicular membrane.

"Posthepatic cholestasis" when used herein refers to a cholestatic liver disease due to obstruction of the large bile ducts.

"Poisoning of the liver" or "hepatotoxicity" or "toxic liver disease" when used herein refer to toxic effects of drugs independent of bile acid accumulation. These drugs penetrate the hepatocytes via the NTCP-mediated transport and cause several direct toxic effects, by damaging the mitochondria or by activating enzymes in the cytochrome P-450 system leading to oxidative stress.

"Drug-induced cholestatic liver disease" when used herein refers to inhibition of the export of bile acids from hepatocytes due to drug effects on bile salt export pump (BSEP).

Drug-induced cholestasis may be caused by several drugs which inhibit BSEP, such as rifampicin, cyclosporine A, rifamycin SV, bosentan, troglitazone, erythromycin estolate, and glibenclamide (Fattinger et al., 2001; Funk et al., 2001; Funk et al., 2001; Stieger et al., 2000; Dawson et al., 2012; Morgan et al., 2010; Ogimura et al., 2011). BSEP is a member of the ATP-binding cassette (ABC) family of transporters (BSEP is also identified as ABCB11) and it is involved in the process of exporting bile acids out of hepatocytes, thus reducing their toxicity to these cells. The above mentioned drugs cause the toxic effects of excess bile acid accumulation because the excretion of bile acid via BSEP is disabled Inhibition of NTCP-mediated bile acid uptake via the lipopeptide-based compound (such as MyrB) and NTCP counterbalances BSEP inhibition, and thereby prevents hepatotoxicity or is suitable for treatment and/or diagnosis.

"Hyperlipidemia" (or hyperlipoproteinemia, or hyperlipidemia) involves abnormally elevated levels of any or all lipids and/or lipoproteins in the blood.

Hyperlipidemias are divided in primary and secondary subtypes. Primary hyperlipidemia is usually due to genetic causes (such as a mutation in a receptor protein), while secondary hyperlipidemia arises due to other underlying causes such as diabetes. Lipid and lipoprotein abnormalities are common in the general population, and are regarded as a modifiable risk factor for cardiovascular disease due to their influence on atherosclerosis.

"Hypercholesterolemia" (or hypercholesterolaemia) is the presence of high levels of cholesterol in the blood. It is a form of "hyperlipidemia".

"Hyperlipidemia" when used herein preferably refers to hypercholesterolemia which includes elevated LDL cholesterol, reduced HDL cholesterol, elevated triglycerides, clogged arteries leading to high blood pressure, cardiovascular disease (CVD), heart attacks and strokes. Preferably, the NTCP-mediated transport is decreased or blocked by the lipopeptide-based compound.

The inventors have found that the lipopeptide MyrB interferes with NTCP-mediated bile salt transport. In particular, MyrB inhibits NTCP-mediated bile salt transport.

Thereby, the $K_i$ for transporter inactivation ($K_i$ for rNTCP~4 nM) is much higher compared to the $IC_{50}$ observed for HBV/HDV infection inhibition (80 pM), which coincides with the finding that HBV infection can already been blocked at concentrations below receptor saturation (Schulze et al., 2010). A plausible explanation is the assumption that similar to other viruses the L-protein/hNTCP complex has to multimerize. Binding of MyrB to a single subunit could abrogate virus entry whereas substrate transport may continue. This assumption is supported by reports demonstrating oligomerization of NTCP (Doring et al., 2012).

Preferably, the lipopeptide-based compound is administered in a therapeutically effective amount.

A "therapeutically effective amount" of a lipopeptide-based compound of this invention refers to the amount that is sufficient to block or inhibit the NTCP-mediated bile salt transport. A "therapeutically effective amount" of a lipopeptide-based compound of this invention further refers to the amount that is sufficient to diagnose, prevent and/or treat the respective liver disease or disorder. The preferred therapeutically effective amount depends on the respective compound that is to be delivered and its respective therapeutic potential.

The lipopeptide-based compound is preferably used in a concentration such that a $K_i$ of about 1 to 10 nM is reached at the target site, i.e. NTCP site (hepatocytes).

In particular, in order to inhibit substrate transport the lipopeptide-based compound is preferably used in a dose such that the concentration at the target site is above the $K_i$ of about 1 to 10 nM.

In case of an $IC_{50}$ value of the lipopeptide-based compound used of about 10 nM, a preferred therapeutically effective amount is about 100 µg per kg body weight or in the range of 1 to 5 mg per patient. The preferred therapeutically effective amount in the range of 1 to 5 mg per patient can be administered once a day or in other embodiments only once every 2-3 days, depending on stability and metabolism of the compound used and the turnover of the complex of NTCP/compound.

A therapeutically effective amount is preferably a daily dosage or a daily administration in the range of
from about 0.1 mg to about 50 mg per patient, i.e. from about 0.0014 mg/kg body weight to about 0.7 mg/kg body weight,
preferably from about 1 mg to about 20 mg per patient, i.e. from about 0.014 mg/kg body weight to about 0.28 mg/kg body weight.

The skilled artisan will be able to determine suitable therapeutically effective amounts.

Preferably, the route of administration or application of the present invention is selected from subcutaneous, intravenous, oral, nasal, intramuscular, transdermal, inhalative, by suppository.

A preferred embodiment for nasal administration or application is a nasal spray.

In one embodiment, the lipopeptide-based compound of the present invention is dissolved in serum from the patient and is applied via injection.

The preferred therapeutically effective amount depends on the respective application and desired outcome of inhibition, diagnosis, prevention and/or treatment.

The lipopeptide-based compounds can be administered/applied in form of pharmaceutical compositions comprising:
at least one lipopeptide-based compound as defined herein above;
and
optionally a pharmaceutically acceptable carrier and/or excipient.

Such pharmaceutical compositions are very well suited for all the uses and methods described herein.

A "pharmaceutically acceptable carrier or excipient" refers to any vehicle wherein or with which the pharmaceutical compositions may be formulated. It includes a saline solution such as phosphate buffer saline. In general, a diluent or carrier is selected on the basis of the mode and route of administration, and standard pharmaceutical practice.

Lipopeptides for Use in the Control of the Cholesterol Level and in Cardiovascular Diseases As discussed above, the present invention provides a lipopeptide-based compound for use in the control or modification of the cholesterol level or cholesterol uptake.

The cholesterol level or uptake is controlled or modified by decreasing or blocking the NCTP-mediated bile salt transport by the lipopeptide-based compound as defined in this application.

As discussed above, the present invention provides a lipopeptide-based compound for use in the diagnosis, prevention and/or treatment of a cardiovascular disease (CVD).

Said uses comprises the control or modification of the cholesterol level or cholesterol uptake, wherein the cholesterol level or uptake is controlled or modified by decreasing or blocking the NCTP-mediated bile salt transport by the lipopeptide-based compound as defined in this application.

Cardiovascular diseases (CVD) are the major cause of morbidity and death in the western world. High levels of cholesterol have been associated with CVD as one of the risc factors. Of particular importance clinically is the abnormal deposition of cholesterol and cholesterol-rich lipoproteins in the coronary arteries. Such deposition, eventually leading to atherosclerosis, is the leading contributory factor in diseases of the coronary arteries. In this case the management of CVD is critical dependent on lipid-lowering therapies. Different classes of drugs are available for this purpose, such as statins, cholesterol absorption inhibitors, bile acid resins, fibrates and nicotinic acid that act by reducing the levels of cholesterol by distinct pathways (Schmitz & Langmann, 2006). These drugs have several side effects and depend on the relative levels of the metabolizing enzymes and transporters that act on cardiovascular drugs.

The main control of cholesterol metabolism is caused by bile acid as an important regulator of cholesterol homeostasis. The levels of bile acid and cholesterol are linked by the regulation of cholesterol metabolism and absorption. The synthesis of the bile acids is the major pathway of cholesterol catabolism in mammals, because the end products of cholesterol utilization are the bile acids. The major pathway for the synthesis of the bile acids is initiated via hydroxylation of cholesterol at the 7 position via the action of cholesterol 7α-hydroxylase (CYP7A1).

That means that the synthesis of bile acids is one of the predominant mechanisms for the excretion of excess cholesterol. Under physiological conditions this regulation is insufficient to compensate for an excess intake of cholesterol. However, if bile acid uptake into hepatocytes is blocked, the excretion of cholesterol in the form of bile acids will be sufficient to compensate for an excess dietary intake of cholesterol. Blocking bile acid uptake via the lipopeptide-based compound according to the invention and NTCP leads to intracellular deficiency of bile acid which is compensated by increased cholesterol metabolism and absorption.

Thus, according to the invention, the lipopeptide-based compounds are suitable for lipid-lowering therapies to prevent CVD.

Assay for NTCP-mediated Transport of Test Compound(s)

As discussed above, the present invention provides an in vitro and in vivo assay or method for testing or measuring the NTCP-mediated transport of test compound(s).

Said in vitro and in vivo assay or method comprises the steps of
(a) providing test compound(s) and a lipopeptide-based compound as defined herein;
(b) providing a test system for functional and selective NTCP expression, which includes measurement of bile acid transport by NTCP;
(c) adding the test compound(s), either together with or without the lipopeptide-based compound, to the NTCP test system of (b);
(d) determining whether the test compound(s) are transported via NTCP by comparing the results of step (b) and (c) each with or without the addition of the lipopeptide-based compound, wherein a test compound is considered being transported via NTCP when the compound(s) decrease, block or inhibit bile salt transport by NTCP (competitive transport) or when the transport of the compound(s) can be decreased, blocked or inhibited by the addition of the lipopeptide-based compound.

The skilled artisan will be able to determine and apply a suitable test system or test model.

Such a suitable test system comprises the functional and selective NTCP expression and thus a functional NTCP transport, which can selectively be blocked/inhibited by a lipopeptide-based compound of the invention (such as MyrB). It can be one or more of the following
a transgenic cell line expressing a functional NTCP,
an transgenic animal expressing a functional NTCP.

Examples for suitable in vitro test systems or test models are:
hepatocyte and hepatoma cell lines stably transduced with an NTCP-encoding lentivirus, as described in the examples and as described in the U.S. Provisional application 61/725,144 filed Nov. 12, 2012.

Examples for suitable in vivo test systems or test models are:
isolated perfused liver, e.g. mouse or rat, as described in vom Dahl et al., 1991 or Schulz et al., 1991;
transgenic mouse, as described in the example and as described in the U.S. Provisional application 61/725, 144 filed Nov. 12, 2012.

Methods for the Treatment of Liver Diseases

As discussed above, the present invention provides a method for the diagnosis, prevention and/or treatment of a liver disease or condition.

Said liver disease or condition is related to sodium taurocholate cotransporting polypeptide (NTCP)-mediated transport of compounds into hepatocytes.

The method of the invention comprises the step of administering a therapeutically effective amount of a lipopeptide-based compound to a patient.

The lipopeptide-based compound is preferably as defined in this application.

Preferably, and as discussed above, said liver disease or condition that is related to NTCP-mediated transport of compounds into hepatocytes, is a liver involved metabolic disease selected from
intrahepatic cholestasis,
poisoning of the liver (by liver toxins)/hepatotoxicity,
drug-induced cholestatic liver disease,
hyperlipidemia,
posthepatic cholestasis.

Preferably, and as discussed above, the compounds which are transported into hepatocytes via NTCP are
bile acids
such as cholate
taurine- or glycine conjugated bile acids and salts thereof
(taurine- or glycine conjugated dihydroxy and trihydroxy bile salts)
such as
taurocholate
glycocho late
taurodeoxycho late
taurochenodeoxycho late
tauroursodeoxycho late
sulfated bile acids and salts thereof
steroides
steroide sulfates
estrogen conjugates (e.g. estrone-3-sulfate, 17α-ethinylestradiol-3-O-sulfate)
dehydroepiandrosterone sulfate
conjugated and non-conjugated thyroid hormones
liver toxins
compounds that are covalently bound to taurocholate (e.g. chlorambucil-taurocholate)
bromosulphophthalein,
drugs
such as
antifungal (e.g. micafungin),
antihyperlipidemic (e.g. simvastatin, rosuvastatin, pitavastatin, fluvastatin, atorvastatin),
antihypertensive,
anti-inflammatory, or
glucocorticoid drugs.

In one embodiment, as discussed above, the NCTP-mediated transport is decreased or blocked by the lipopeptide-based compound.

Preferably, and as discussed above, the therapeutically effective amount of the lipopeptide-based compound is in the range of from about 0.1 mg to about 50 mg per patient and per day, preferably from about 1 mg to about 20 mg per patient per day.

Methods for Controlling the Cholesterol Level and Treatment of Cardiovascular Diseases As discussed above, the present invention provides a method for the control or modification of the cholesterol level or cholesterol uptake.

The cholesterol level or uptake is controlled or modified by decreasing or blocking the NCTP-mediated bile salt transport (by the lipopeptide-based compound).

The method of the invention comprises the step of administering a therapeutically effective amount of a lipopeptide-based compound to a patient.

The lipopeptide-based compound is preferably as defined in this application.

As discussed above, the present invention provides a method for the diagnosis, prevention and/or treatment of a cardiovascular disease (CVD),
comprising administering a therapeutically effective amount of a lipopeptide-based compound, preferably as defined in any of claims 5 to 9, to a patient.

Thereby, the cholesterol level or uptake is preferably controlled or modified by decreasing or blocking the NCTP-mediated bile salt transport by the lipopeptide-based compound as defined in this application.

NTCP-mediated blocking bile acid uptake enables to an elevated cholesterol turn over via hepatocytes. Hence LDL cholesterol will be reduced and HDL cholesterol will be elevated. As a consequence the risk of clogged arteries leading to high blood pressure, CVD heart attacks and strokes will be minimized.

Further Description of the Invention

The inventors show that the lipopeptide Myrcludex B (MyrB) interferes with NTCP-mediated bile salt transport. MyrB:

Myr-GTNLSVPNPLGFFPDHQLDPAFGANSNNPDWDFNPNKDHWPEANKV

G-amide

Functional analyses of the NTCP/SLC10A receptor revealed that:
(i) human NTCP (hNTCP) binds MyrB;
(ii) NTCP-substrates interfere with HBV infection;
(iii) MyrB inhibits NTCP-mediated bile salt transport.

MyrB is an interesting novel drug to target NTCP, but also to study its function in vivo.

Remarkably, the $K_i$ for transporter inactivation (K, for rNTCP~4 nM) is much higher compared to the $IC_{50}$ observed for HBV/HDV infection inhibition (80 pM) (Schulze et al., 2010). This coincides with the finding that HBV infection can already been blocked at concentrations below receptor saturation (Schulze et al., 2010). A plausible explanation is the assumption that similar to other viruses the L-protein/hNTCP complex has to multimerize. If only one subunit bound MyrB, entry may be abrogated although substrate transport may progress. This assumption is supported by reports demonstrating oligomerization of NTCP (Doring et al., 2012). The observation that natural substrates of NTCP, when applied at high concentrations (FIGS. 2C and D) interfere with MyrB binding and HBV infection indicate that sodium driven transport is coupled to effective HBV entry.

The following examples and drawings illustrate the present invention without, however, limiting the same thereto.

BRIEF DESCRIPTION OF THE DRAWINGS

FIG. 1 hNTCP specifically binds lipopeptide MyrB.
Stable human NTCP (hNTCP) expression in five hepatoma cell lines was accomplished by lentiviral transduction following antibiotic selection.
(A) Western Blots of deglycosylated cell lysates from HuH7$^{hNTCP}$, HepG2$^{hNTCP}$, HepaRG$^{hNTCP}$ Hepa1-6$^{hNTCP}$ and Hep56.1D$^{hNTCP}$ cell lines in comparison to mock-transduced cells and two PHH samples. Only 10% of sample was loaded on the HepaRG$^{hNTCP}$ lane (*).
(B-C) hNTCP expressing human cell lines were incubated with the Atto488-labeled peptide MyrB$^{atto}$ (green or 488λ). Peptide binding was analysed by co-localisation of the peptide with hNTCP-IF using an hNTCP-specific antibody (red) (B) or FACS using the mutant peptide MyrB$^{attoAla11-15}$ or an excess of unlabeled MyrB (C).
(D) FACS analysis of MyrB binding as described in (C) for the HepG2$^{mNtcp}$ cell lines.
(E) HepG2 ratNtcp-eGFP expressing cells (green) were incubated with MyrB$^{atto}$ (red) and analysed by confocal microscopy. Note the co-localisation of hNTCP/MyrB$^{atto}$ in microvilli.

Figure 2A:
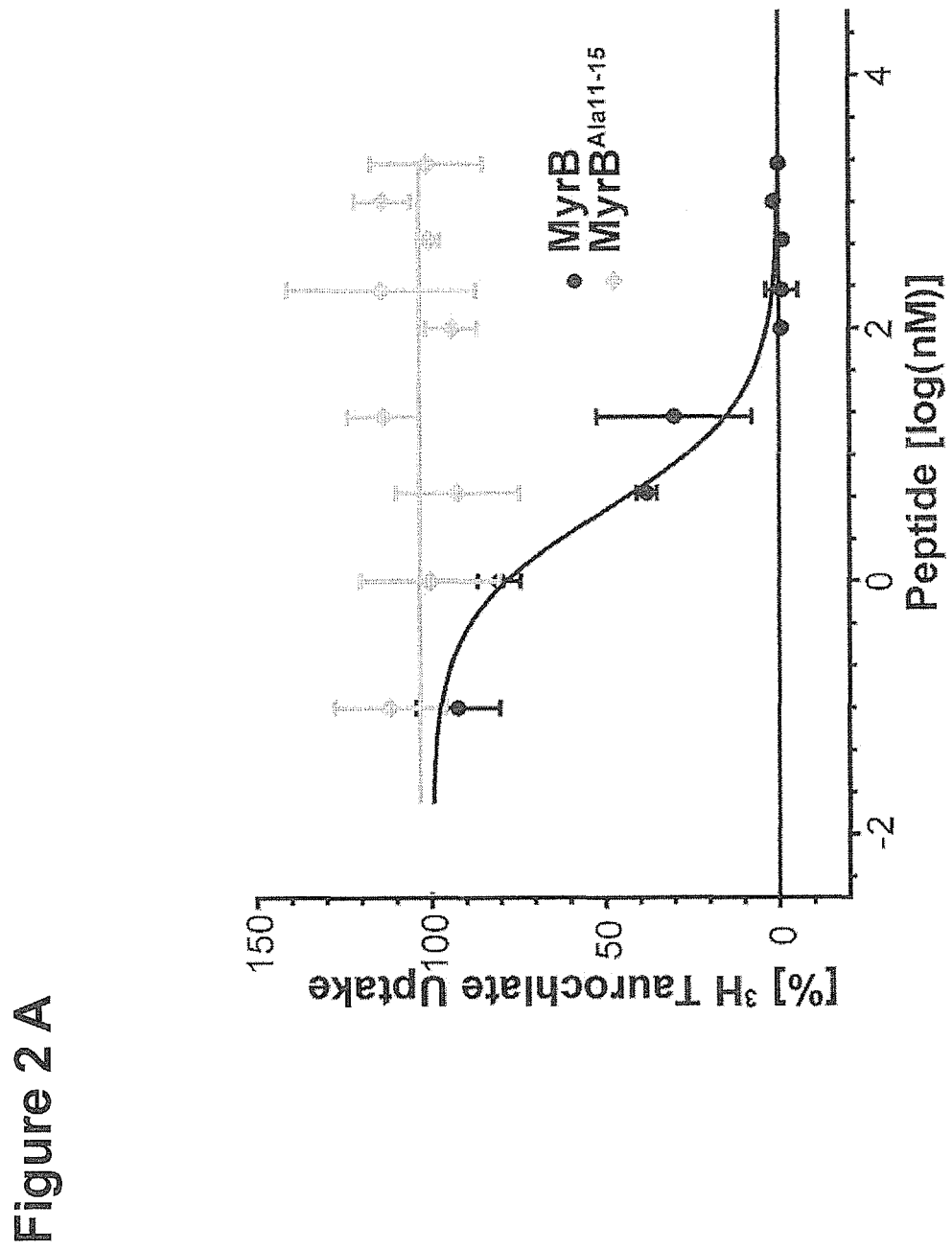
FIG. 2 Influence of lipopeptide MyrB on NTCP-mediated bile acid transport; effect of bile acids on HBV infection.
(A) rNtcp-eGFP expressing HepG2 cells were incubated with increasing concentrations of MyrB or mutant MyrB$^{Ala11-15}$ (a mutant with Ala mutations in the region 9-NPLGFFP-15 (amino acid positions 20-26 of SEQ ID NO: 2), namely 9-NPAAAAA-15 amino acid positions 8-14 of SEQ ID NO:21)) and $^3$H-taurocholate uptake was quantified. Uncompeted uptake was set to 100%.
Figure 2:
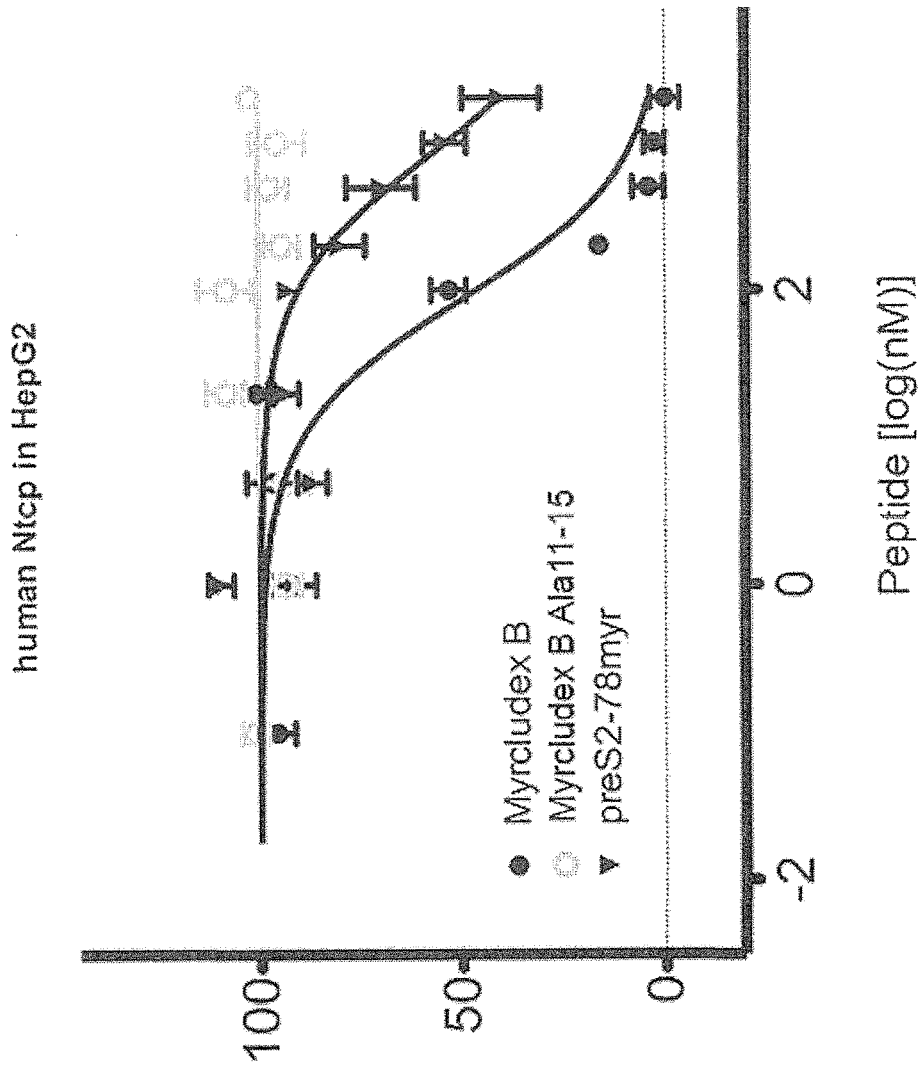

(B) hNtcp-eGFP expressing HepG2 cells were incubated with increasing concentrations of MyrB, mutant MyrB$^{Ala11-15}$ (or preS2-78myr and $^3$H-taurocholate uptake was quantified. Uncompeted uptake was set to 100%.

(C-D) Differentiated HepaRG (B) or HuH7$^{hNTCP}$ cells (C) were preincubated 2 h before and coincubated during HBV infection with 5, 50 and 500 µM TC, TDC or TCDC and secreted HBeAg was determined d7-9 p.i. Infection was controlled by addition of MyrB 2 h prior to and during infection.

(E) HuH7$^{hNTCP}$ cells were incubated at the indicated bile salt concentrations overnight at 37° C., trypsinized and incubated in the presence of bile salts with MyrB$^{atto}$ for further 30 min. Binding was quantified by FACS analysis. Untagged MyrB was used as a control.

EXAMPLES

1. Methods 1.1 Plasmids: hNTCP cDNA (Origene, USA) and mNtcp cDNA (Rose et al., 2011) were subcloned into the puromycin co-expressing lentiviral vector pWPI-puro. hNTCP, mNtcp and h/mNtcp chimera were generated by overlapping PCR and introduced into pWPI-GFP.

1.2 Cells: Lentiviruses were produced and used to transduce hNTCP into human (HepaRG, HepG2, HuH7), mouse (Hepa1-6, Hep56.1D) and the rat hepatoma cell line TC5123. The respective mock transduced cells were used as controls. To generate stable cell lines, selection with 2.5 µg/ml puromycin was achieved. Differentiation of transduced HepaRG was induced by DMSO as described (Gripon et al., 2002). HepG2-rNTCP and HepG2-rNTCP-eGFP cell line have been described previously for expression of rat Ntcp with or without fused eGFP (Stross et al., 2010).

1.3 Synthesis and Labeling of Peptides: Synthesis of MyrB and the MyrB mutant and the control peptide preS2-78myr was performed by solid phase synthesis (Schieck et al., 2013). Labelling was achieved by coupling atto565-NHS-ester/atto488-NHS-ester (ATTO-TEC, Germany) to the lysine residues of the peptides. Monolabelled peptides were pooled after HPLC purification and stock solutions (100 µM) were prepared and stored at −80° C.

MyrB
SEQ ID NO: 18
Myr-GTNLSVPNPLGFFPDHQLDPAFGANSNNPDWDFNPNKDHWPEANKV
G-amide mutant MyrB$^{Ala11-15}$
SEQ ID NO: 21
Myr-GTNLSVPNPAAAAADHQLDPAFGANSNNPDWDFNPNKDHWPEANKV
G-amide preS2-78myr
SEQ ID NO: 22
Myr-gqnlstsnplgffpdhqldpafrantanpdwdfnpnkdtwpdankv
gagafglgftpphggllgwspqaqgilqtlp 1.4 Flow Cytometry: Cells were incubated for 30 min at 37° C. in medium containing 200 nM MyrB$^{atto}$ or the MyrB$^{atto}$-mutant. Cells were washed (PBS/1% BSA), trypsinized, and suspended in Krebs-Henseleit-Buffer. Flow cytometry was performed on a FACS Canto II (BD Bioscience, Heidelberg, Germany); FlowJo v7.61 software (Treestar, Ashton, USA) was used for analysis. Compensation was performed using BD Compbeats (BD Bioscience, Heidelberg, Germany).

1.5 IF: Cells were grown on coverslips (see Meier et al., 2012) washed and incubated with 400 nM MyrB (37° C.; 30 min). Cells were washed again (3×PBS/2% BSA), fixed with PFA, washed with PBS/lug/ml Hoechst 3342 and mounted (FluoromountG). NTCP immune staining was achieved after permeabilisation (10 min/RT) with TritonX 100 using a α-SCL10A1/NTCP antibody (Sigma, Germany) diluted 1:750 in PBS/2% BSA (18 h at 4° C.). A polyclonal rabbit antiserum H863 was used for HBcAg-staining, a polyclonal rabbit antiserum for MRP-2 detection, patient-derived serum (M. Roggendorf, Essen) for HδAg. As secondary antibodies goat anti-rabbit or human, labelled with either AlexaFluor488 or AlexaFluor546 (Invitrogen) was used. Actin staining was performed by the addition of atto633-labelled Phalloidin diluted 1:2000 (ATTO-Tec, Germany) to the second staining step. Images were taken on a Leica DM IRB or Leica SP2 confocal microscope (Leica, Germany), image analysis was performed using ImageJ.

1.6 Taurocholate uptake assay: HepG2-rNtcp cells were used for studying [3H] TC uptake as described before (Kubitz et al., 2004). Briefly, HepG2-rNtcp cells were cultured for 12 h (in D-MEM/Ham's F12 w. 10% FCS medium containing G418 for selection) were preincubated with increasing concentrations of MyrB for 20 min before addition of TC (150 µM containing 450 cpm/fmol [3H]TC). Uptake was stopped after 5 min by removing the medium and washing thrice with ice-cold PBS. Cells were lysed (0.2 M NaOH and 0.05% SDS). Radioactivity of cell lysates was measured in a liquid scintillation counter (Packard instruments, Frankfurt, Germany) using Ultima Gold liquid scintillation solution (Perkin Elmer, Rodgau, Germany).

1.7 Western blotting: Whole cell lysates were treated with PNGase F (New England Biolabs) and analyzed by Western blot using rabbit anti-hNTCP antibody (Sigma-Aldrich, or the anti-serum K9.

2. Binding of Lipopeptide MyrB to hNTCP

To assess whether expression of hNTCP facilitates MyrB-binding, HuH7-, HepG2-, HepaRG- and the two mouse hepatoma cells Hepa1-6 and Hep56.1D were stably transduced with an hNTCP-encoding lentivirus. hNTCP expression was verified by Western Blot (FIG. 1A).

HuH7$^{hNTCP}$, HepG2$^{hNTCP}$, Hepa1-6$^{hNTCP}$ and Hep56.1D$^{hNTCP}$ express comparable amounts of hNTCP. HepaRG$^{hNTCP}$-expression was higher for unknown reasons. No hNTCP was detected in mock-transduced cells. To examine whether hNTCP-expression renders HuH7$^{hNTCP}$, HepG2$^{hNTCP}$ and HepaRG$^{hNTCP}$ cells capable of binding HBVpreS we analysed cell association of atto-dye-labeled MyrB (MyrB$^{atto}$) by fluorescence microscopy (FIG. 1B) and flow cytometry (FIG. 1C). Specificity was controlled through MyrB-competition and the MyrB$^{attoAla11-15}$ mutant. hNTCP-expression resulted in specific MyrB-binding indicating a valid role of hNTCP as an HBVpreS-specific receptor.

Since hepatocytes from some non-HBV susceptible species (mice(m), rats(r)) bind MyrB (Meier et al., 2012) and accumulate the peptide in the liver after injection (Schieck et al., 2013), we expected that mNtcp and rNtcp also bind MyrB. We therefore used HepG2$^{mNtcp}$ cells and HepG2 cells expressing a ratNTCP-eGFP-fusion and analysed MyrB$^{atto}$ binding. We verified specific and competable binding of MyrB$^{atto}$ to both cell lines (FIGS. 1D and E). Taking advantage of the fluorescence of the ratNTCP-eGFP fusion, we confirmed co-localisation of the MyrB/rNtcp-complex in microvilli.

3. Inhibition of Bile Salt Transport 3.1 Lipopeptide MyrB Inhibits the Bile Salt Transporter Function of NTCP.

The mere size of MyrB as a specific ligand for some NTCPs suggests that several contact sites are involved in binding. To test whether MyrB therefore interferes with the bile salt transporter function of NTCPs, we analysed interference of MyrB with uptake of $^3$H-labeled taurocholate in Flag-rNtcp-eGFP expressing HepG2 cell lines. MyrB inhibited rNtcp with an IC$_{50}$ of 4 nM (FIG. 2A). Remarkably, the IC$_{50}$s for inhibition of HBV infection (~100 pM) and of bile salt transport (~5 nM) differ substantially which relates to observations that infection inhibition does not require binding saturation of NTCP (Schulze et al., 2010).

We furthermore analysed interference of MyrB with uptake of $^3$H-labeled taurocholate in Flag-hNtcp-eGFP expressing HepG2 cell lines in comparison to two control peptides: mutant myrB$^{Ala11-15}$ (a mutant with Ala mutations in the region 9-NPLGFFP-15 (amino acid positions 20-26 of SEQ ID NO:2), namely 9-NPAAAAA-15 (amino acid positions 8-14 of SEQ ID NO:21)) and preS2-78myr (see FIG. 2B).

mutant MyrB$^{Ala11-15}$
SEQ ID NO: 21
Myr-GTNLSVPNPAAAAADHQLDPAFGANSNNPDWDFNPNKDHWPEANKV G-amide preS2-78myr
SEQ ID NO: 22
Myr-gqnlstsnplgffpdhqldpafrantanpdwdfnpnkdtwpdankv gagafglgftpphggllgwspqaqgilqtlp 3.2 NTCP Substrates Taurocholate (TC), Taurodeoxycholate (TDC) and Taurochenodeoxy-Cholate (TCDC) Inhibit HBV Infection.

Figure 2E:
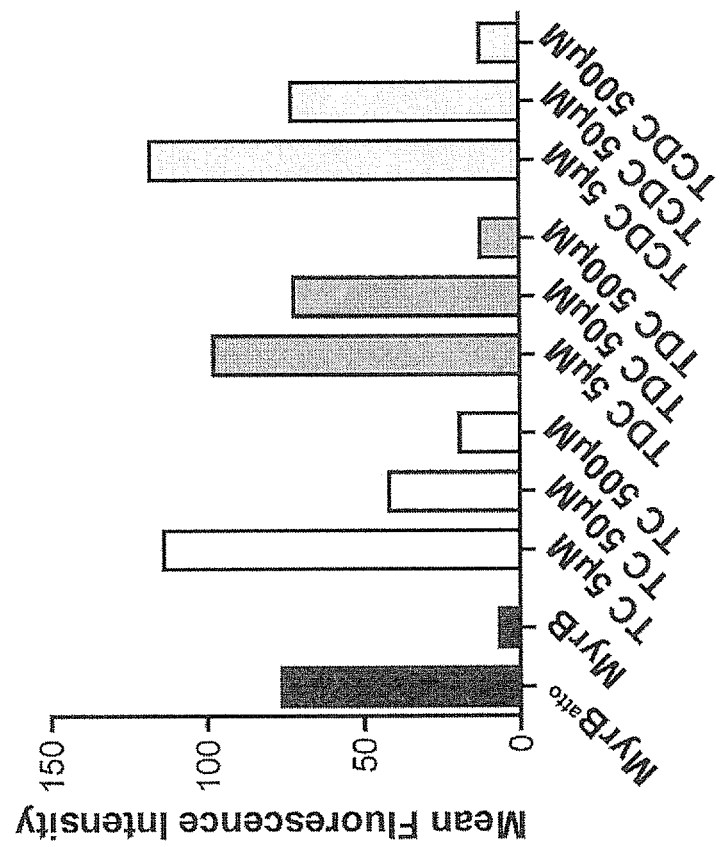

To test if natural substrates of NTCP affect HBV infection, differentiated HepaRG (FIG. 2C) and HuH7$^{hNTCP}$ (FIG. 2D) cells were inoculated with HBV at increasing concentrations of TC, TDC and TCDC. All three substrates inhibited HBV-infection at non-physiological concentrations (50 µM and 500 µM) in both cell lines as shown by HBeAg secretion. Marginal reduction was observed at 5 µM indicating that under physiological conditions (<5 µM) hNTCP remains a functional HBV/HDV receptor. To test if TC, TDC and TCDC interferes with MyrB$^{atto}$-binding we performed a binding competition assay (FIG. 2E). In the presence of 500 µM all substrates profoundly interfered with preS-binding.

The features disclosed in the foregoing description, in the claims and/or in the accompanying drawings may, both separately and in any combination thereof, be material for realizing the invention in diverse forms thereof.

REFERENCES

Craddock A. L., Love, M. W., Daniel, R. W., Kirby, L. C., Walters, H. C., Wong, M. H., and Dawson, P. A. (1998) Am. J. Physiol 274, G157-G169.

Dawson S, et al. (2012) In vitro inhibition of the bile salt export pump correlates with risk of cholestatic drug-induced liver injury in humans. *Drug Metab Dispos* 40: 130-138.

Doring B, Lutteke T, Geyer J, Petzinger E. The SLC10 carrier family: transport functions and molecular structure. Curr Top Membr 2012; 70:105-168.

Dong Z, Ekins S, Polli J E. Structure—Activity Relationship for FDA Approved Drugs As Inhibitors of the Human Sodium Taurocholate Cotransporting Polypeptide (NTCP). Mol. Pharmaceutics 2013, 10, 1008-1019.

Fattinger K, Funk C, Pantze M, et al. The endothelin antagonist bosentan inhibits the canalicular bile salt export pump: a potential mechanism for hepatic adverse reactions. Clin Pharmacol Ther. 2001; 69:223-31.

Friesema E C, Docter R, Moerings E P, Stieger B, Hagenbuch B, Meier P J, Krenning E P, Hennemann G, Visser T J (1999) Identification of thyroid hormone transporters. Biochem Biophys Res Commun 254:497-501.

Funk C, Pantze M, Jehle L, et al. Troglitazone-induced intrahepatic cholestasis by an interference with the hepatobiliary export of bile acids in male and female rats. Correlation with the gender difference in troglitazone sulfate formation and the inhibition of the canalicular bile salt export pump (Bsep) by troglitazone and troglitazone sulfate. Toxicology. 2001; 167:83-98.

Funk C, Ponelle C, Scheuermann G, et al. Cholestatic potential of troglitazone as a possible factor contributing to troglitazone-induced hepatotoxicity: in vivo and in vitro interaction at the canalicular bile salt export pump (Bsep) in the rat. Mol Pharmacol. 2001; 59:627-35.

Gripon P, Rumin S, Urban S, LeSeyec J, Glaise D, Cannie I, Guyomard C, Lucas J, Trepo C, Guguen-Guillouzo C. Infection of a human hepatoma cell line by hepatitis B virus. Proc Natl Acad Sci USA 2002; 99:15655-15660.

Gripon P, Cannie I, Urban S. Efficient inhibition of hepatitis B virus infection by acylated peptides derived from the large viral surface protein. J Virol 2005; 79:1613-1622.

Hagenbuch B, Meier P J. Molecular cloning, chromosomal localization, and functional characterization of a human liver Na+/bile acid cotransporter. J. Clin. Invest., 93 (1994), pp. 1326-1331.

Ho R H, Tirona R G, Leake B F, Claeser H, Lee W, Lemke C J, Wang Y, Kim R B. Drug and acid transporters in rosuvastatin hepatic upatke: function, expression and pharmacogenetics. Gastroenterology, 130 (6) (2006), pp. 1793-1806

Kotani N, Maeda K, Debori Y, Camus S, Li R, Chesne C, Sugiyama Y. Expression and Transport Function of Drug Uptake Transporters in Differentiated HepaRG Cells. Mol Pharm 2012.

Kramer W, Stengelin S, Baringhaus K H, Enhsen A, Heuer H, Becker W, Corsiero D, Girbig F, Noll R, Weyland C (1999) Substrate specificity of the ileal and the hepatic Na(+)/bile acid cotransporters of the rabbit. I. Transport studies with membrane vesicles and cell lines expressing the cloned transporters. J Lipid Res 40:1604-1617.

Kubitz R, Saha N, Kuhlkamp T, Dutta S, Vom D S, Wettstein M, Haussinger D. Ca2+-dependent protein kinase C iso forms induce cholestasis in rat liver. J Biol Chem 2004; 279:10323-10330.

Kullak-Ublick, G A. Drug-Induced Cholestatic Liver Disease. Madame Curie Bioscience Database [Internet]. Austin (Tex.): Landes Bioscience; 2000. Bookshelf I D: NBK6102.

Meier A, Mehrle S, Weiss T S, Mier W, Urban S. The myristoylated preS1-domain of the hepatitis B virus L-protein mediates specific binding todifferentiated hepatocytes. Hepatology 2013; 58(1): 31-42. [Epub ahead of print: 2012. Dec. 5.]

Morgan R E, et al. (2010) Interference with bile salt export pump function is a susceptibility factor for human liver injury in drug development. Toxicol Sci 118: 485-500.

Ogimura E, et al. (2011) Bile salt export pump inhibitors are associated with bile acid-dependent drug-induced toxicity in sandwich-cultured hepatocytes. Biochem Biophys Res Commun 416: 313-317.

Rose A J, Berriel Diaz M, Reimann A, Klement J, Walcher T, Krones-Herzig A, Strobel O, Werner J, Peters A, Kleyman A, Tuckermann J P, Vegiopoulos A, Herzig S. Molecular control of systemic bile acid homeostasis by the liver glucocorticoid receptor. Cell Metab. 2011; 14(1): 123-30.

Schieck A, Schulze A, Gahler C, Muller T, Haberkorn U, Alexandrov A, Urban S, Mier W. Hepatitis B virus hepatotropism is mediated by specific receptor recognition in the liver and not restricted to susceptible hosts. Hepatology 2013; 58(1): 43-53. [Epub ahead of print: 2013. Jan. 4.]

Schmitz G., Langmann T. Pharmacogenomics of cholesterol lowering therapy. Vasc. Pharmacol. (2006) 44: 75-89.

Schroeder A, Eckhardt U, Stieger B, Tynes R, Schteingart C D, Hofmann A F, Meier P J, Hagenbuch B (1998) Substrate specificity of the rat liver Na(+)-bile salt cotransporter in *Xenopus laevis* oocytes and in CHO cells. Am J Physiol 274:G370-G375.

Schulz W A, Eickelmann P, Hallbrucker C, Sies H, Häussinger D. Increase of beta-actin mRNA upon hypotonic perfusion of perfused rat liver. FEBS Lett. 1991; 292(1-2):264-6.

Schulze A, Schieck A, Ni Y, Mier W, Urban S. Fine mapping of pre-S sequence requirements for hepatitis B virus large envelope protein-mediated receptor interaction. J Virol 2010; 84:1989-2000.

Stieger B, Fattinger K, Madon J, et al. Drug- and estrogen-induced cholestasis through inhibition of the hepatocellular bile salt export pump (Bsep) of rat liver. Gastroenterology. 2000; 118:42230.

Stross C, Helmer A, Weissenberger K, Gorg B, Keitel V, Haussinger D, Kubitz R. Protein kinase C induces endocytosis of the sodium taurocholate cotransporting polypeptide. Am J Physiol Gastrointest Liver Physiol 2010; 299:G320-G328.

Trauner M and Boyer J L. Bile Salt Transporters: Molecular Characterization, Function, and Regulation. Physiol Rev Apr. 1, 2003 83:633-671.

Urban S, *Future Virol.* 2008, 3(3), 253-264.

vom Dahl S, Hallbrucker C, Lang F, Häussinger D. Regulation of cell volume in the perfused rat liver by hormones. Biochem J. 1991, 280:105-9.

Yan H, Zhong G, Xu G, He W, Jing Z, Gao Z, Huang Y, Qi Y, Peng B, Wang H, Fu L, Song M, Chen P, Gao W, Ren B, Sun Y, Cai T, Feng X, Sui J, Li W. Sodium taurocholate cotransporting polypeptide is a functional receptor for human hepatitis B and D virus. elife 2012; 1:e00049. Epub 2012 Nov. 13.

Yanni S B, Augustijns P F, Benjamin Jr. D K, Brouwer K L, Thakker D R, Annaert P P. In vitro investigation of the hepatobiliary disposition mechanisms of the antifungal agent micafungin in humans and rats. Drug Metab. Dispos., 38 (2010), pp. 1848-1856

---

The invention claimed is:

1. A method for treating a cardiovascular disease (CVD) in a patient, the method comprising administering a therapeutically effective amount of a lipopeptide to the patient,
   wherein the lipopeptide comprises the sequence selected from SEQ ID NOs: 2 to 12, 14, 18 to 20, and 22, and wherein the lipopeptide comprises an N-terminal myristoylation and a C-terminal hydrophobic modification.

2. The method of claim 1, wherein said administering the lipopeptide causes control or modification of cholesterol level or cholesterol uptake, and
   wherein the cholesterol level or uptake is controlled or modified by decreasing or blocking the NCTP-mediated bile salt transport by the lipopeptide.

3. The method of claim 1, comprising administering the lipopeptide via a route selected from subcutaneous, intravenous, oral, nasal, intramuscular, transdermal, inhalative, and suppository.

4. A method for reducing taurocholate uptake in liver cells of a human, the method comprising administering to the human an effective amount of a lipopeptide comprising the sequence selected from SEQ ID NOs: 2 to 12, 14, 18 to 20, and 22, and wherein the lipopeptide comprises an N-terminal myristoylation and a C-terminal hydrophobic modification.

5. The method of claim 4, comprising administering the lipopeptide via a route selected from subcutaneous, intravenous, oral, nasal, intramuscular, transdermal, inhalative, and suppository.

6. The method of claim 1, wherein the C-terminal hydrophobic modification comprises conjugation of the lipopeptide to a moiety selected from cholesterol, phospholipid, gycolipid, glycerol ester, steroid, ceramid, isoprene, adamantine, fernesol, aliphatic group, polyaromatic compound, acyl group, bile salt, and a bile salt conjugate.

7. The method of claim 6, wherein the acyl group is oleic acid.

8. The method of claim 6, wherein the C-terminal hydrophobic modification comprises conjugation of the lipopeptide to the moiety via a covalent bond.

9. The method of claim 8, wherein the covalent bond is a carbamate, amide, ether, or disulfide bond.

10. The method of claim 1, wherein the lipopeptide comprises the sequence of SEQ ID NO: 18.

11. The method of claim 1, wherein the lipopeptide comprises the sequence of SEQ ID NO: 19.

12. The method of claim 1, wherein the lipopeptide comprises the sequence of SEQ ID NO: 20.

13. The method of claim 4, wherein the C-terminal hydrophobic modification comprises conjugation of the lipopeptide to a moiety selected from cholesterol, phospholipid, gycolipid, glycerol ester, steroid, ceramid, isoprene, adamantine, fernesol, aliphatic group, polyaromatic compound, acyl group, bile salt, and a bile salt conjugate.

14. The method of claim 13, wherein the acyl group is oleic acid.

15. The method of claim 13, wherein the C-terminal hydrophobic modification comprises conjugation of the lipopeptide to the moiety via a covalent bond.

16. The method of claim 15, wherein the covalent bond is a carbamate, amide, ether, or disulfide bond.

17. The method of claim 4, wherein the lipopeptide comprises the sequence of SEQ ID NO: 18.

18. The method of claim 4, wherein the lipopeptide comprises the sequence of SEQ ID NO: 19.

19. The method of claim 4, wherein the lipopeptide comprises the sequence of SEQ ID NO: 20.

* * * * *

SEQUENCE LISTING

```
<160> NUMBER OF SEQ ID NOS: 22

<210> SEQ ID NO 1
<211> LENGTH: 7
<212> TYPE: PRT
<213> ORGANISM: Hepatitis B virus
<220> FEATURE:
<221> NAME/KEY: misc_feature
<222> LOCATION: (6)..(6)
<223> OTHER INFORMATION: Xaa can be any naturally occurring amino acid

<400> SEQUENCE: 1

Asn Pro Leu Gly Phe Xaa Pro
1               5

<210> SEQ ID NO 2
<211> LENGTH: 119
<212> TYPE: PRT
<213> ORGANISM: Hepatitis B virus

<400> SEQUENCE: 2

Met Gly Gly Trp Ser Ser Lys Pro Arg Lys Gly Met Gly Thr Asn Leu
1               5                   10                  15

Ser Val Pro Asn Pro Leu Gly Phe Phe Pro Asp His Gln Leu Asp Pro
            20                  25                  30

Ala Phe Gly Ala Asn Ser Asn Asn Pro Asp Trp Asp Phe Asn Pro Ile
        35                  40                  45

Lys Asp His Trp Pro Gln Ala Asn Gln Val Gly Val Gly Ala Phe Gly
    50                  55                  60

Pro Gly Phe Thr Pro Pro His Gly Gly Val Leu Gly Trp Ser Pro Gln
65                  70                  75                  80
```

Ala Gln Gly Ile Leu Ala Thr Val Pro Ala Met Pro Pro Pro Ala Ser
            85                  90                  95

Thr Asn Arg Gln Ser Gly Arg Gln Pro Thr Pro Ile Ser Pro Pro Leu
        100                 105                 110

Arg Asp Ser His Pro Gln Ala
        115

<210> SEQ ID NO 3
<211> LENGTH: 119
<212> TYPE: PRT
<213> ORGANISM: Hepatitis B virus

<400> SEQUENCE: 3

Met Gly Gly Trp Ser Ser Lys Pro Arg Lys Gly Met Gly Thr Asn Leu
1               5                   10                  15

Ser Val Pro Asn Pro Leu Gly Phe Phe Pro Asp His Gln Leu Asp Pro
            20                  25                  30

Ala Phe Lys Ala Asn Ser Glu Asn Pro Asp Trp Asp Leu Asn Pro His
        35                  40                  45

Lys Asp Asn Trp Pro Asp Ala His Lys Val Gly Val Gly Ala Phe Gly
    50                  55                  60
Pro Gly Phe Thr Pro Pro His Gly Gly Leu Leu Gly Trp Ser Pro Gln
65                  70                  75                  80

Ala Gln Gly Ile Leu Thr Ser Val Pro Ala Ala Pro Pro Pro Ala Ser
            85                  90                  95

Thr Asn Arg Gln Ser Gly Arg Gln Pro Thr Pro Leu Ser Pro Pro Leu
        100                 105                 110

Arg Asp Thr His Pro Gln Ala
        115

<210> SEQ ID NO 4
<211> LENGTH: 119
<212> TYPE: PRT
<213> ORGANISM: Hepatitis B virus

<400> SEQUENCE: 4

Met Gly Gly Trp Ser Ser Lys Pro Arg Lys Gly Met Gly Thr Asn Leu
1               5                   10                  15

Ser Val Pro Asn Pro Leu Gly Phe Phe Pro Asp His Gln Leu Asp Pro
            20                  25                  30

Ala Phe Lys Ala Asn Ser Glu Asn Pro Asp Trp Asp Leu Asn Pro His
        35                  40                  45

Lys Asp Asn Trp Pro Asp Ala His Lys Val Gly Val Gly Ala Phe Gly
    50                  55                  60

Pro Gly Phe Thr Pro Pro His Gly Gly Leu Leu Gly Trp Ser Pro Gln
65                  70                  75                  80

Ala Gln Gly Ile Leu Thr Ser Val Pro Ala Ala Pro Pro Pro Ala Ser
            85                  90                  95

Thr Asn Arg Gln Ser Gly Arg Gln Pro Thr Pro Leu Ser Pro Pro Leu
        100                 105                 110

Arg Asp Thr His Pro Gln Ala
        115

<210> SEQ ID NO 5
<211> LENGTH: 108
<212> TYPE: PRT
<213> ORGANISM: Hepatitis B virus

<400> SEQUENCE: 5

Met Gly Gln Asn Leu Ser Thr Ser Asn Pro Leu Gly Phe Phe Pro Glu
1               5                   10                  15

His Gln Leu Asp Pro Ala Phe Lys Ala Asn Thr Asn Asn Pro Asp Trp
            20                  25                  30

Asp Phe Asn Pro Lys Lys Asp Tyr Trp Pro Glu Ala Asn Lys Val Gly
        35                  40                  45

Ala Gly Ala Phe Gly Pro Gly Phe Thr Pro Pro His Gly Gly Leu Leu
    50                  55                  60

Gly Trp Ser Pro Gln Ala Gln Gly Ile Leu Thr Thr Leu Pro Ala Asn
65                  70                  75                  80

Pro Pro Pro Ala Ser Thr Asn Arg Gln Ser Gly Arg Gln Pro Thr Pro
                85                  90                  95

Leu Ser Pro Pro Leu Arg Asp Thr His Pro Gln Ala
            100                 105

<210> SEQ ID NO 6
<211> LENGTH: 107
<212> TYPE: PRT
<213> ORGANISM: Hepatitis B virus

<400> SEQUENCE: 6

Met Gly Gln Asn Leu Ser Thr Ser Asn Pro Leu Gly Phe Phe Pro Asp
1               5                   10                  15

His Gln Leu Asp Pro Ala Phe Arg Ala Asn Thr Asn Asn Pro Asp Trp
            20                  25                  30

Asp Phe Asn Pro Asn Lys Asp Thr Trp Pro Asp Ala Asn Lys Val Gly
        35                  40                  45

Ala Gly Ala Phe Gly Leu Gly Phe Thr Pro Pro His Gly Gly Leu Leu
    50                  55                  60

Gly Trp Ser Pro Gln Ala Gln Gly Phe Gln Thr Leu Pro Ala Asn Pro
65                  70                  75                  80

Pro Pro Ala Ser Thr Asn Arg Gln Ser Gly Arg Gln Pro Thr Pro Leu
                85                  90                  95

Ser Pro Pro Leu Arg Thr Thr His Pro Gln Ala
            100                 105

<210> SEQ ID NO 7
<211> LENGTH: 118
<212> TYPE: PRT
<213> ORGANISM: Hepatitis B virus

<400> SEQUENCE: 7

Met Gly Leu Ser Trp Thr Val Pro Leu Glu Trp Gly Lys Asn Ile Ser
1               5                   10                  15

Thr Thr Asn Pro Leu Gly Phe Phe Pro Asp His Gln Leu Asp Pro Ala
            20                  25                  30

Phe Arg Ala Asn Thr Arg Asn Pro Asp Trp Asp His Asn Pro Asn Lys
        35                  40                  45

Asp His Trp Thr Glu Ala Asn Lys Val Gly Val Gly Ala Phe Gly Pro
    50                  55                  60

Gly Phe Thr Pro Pro His Gly Gly Leu Leu Gly Trp Ser Pro Gln Ala
65                  70                  75                  80

Gln Gly Met Leu Lys Thr Leu Pro Ala Asp Pro Pro Ala Ser Thr
                85                  90                  95

Asn Arg Gln Ser Gly Arg Gln Pro Thr Pro Ile Thr Pro Pro Leu Arg

```
                    100                 105                 110

Asp Thr His Pro Gln Ala
        115

<210> SEQ ID NO 8
<211> LENGTH: 119
<212> TYPE: PRT
<213> ORGANISM: Hepatitis B virus

<400> SEQUENCE: 8

Met Gly Ala Pro Leu Ser Thr Thr Arg Arg Gly Met Gly Gln Asn Leu
1               5                   10                  15

Ser Val Pro Asn Pro Leu Gly Phe Phe Pro Asp His Gln Leu Asp Pro
            20                  25                  30

Leu Phe Arg Ala Asn Ser Ser Ser Pro Asp Trp Asp Phe Asn Thr Asn
        35                  40                  45

Lys Asp Ser Trp Pro Met Ala Asn Lys Val Gly Val Gly Gly Tyr Gly
    50                  55                  60

Pro Gly Phe Thr Pro Pro His Gly Gly Leu Leu Gly Trp Ser Pro Gln
65                  70                  75                  80

Ala Gln Gly Val Leu Thr Thr Leu Pro Ala Asp Pro Pro Pro Ala Ser
                85                  90                  95

Thr Asn Arg Arg Ser Gly Arg Lys Pro Thr Pro Val Ser Pro Pro Leu
            100                 105                 110

Arg Asp Thr His Pro Gln Ala
        115

<210> SEQ ID NO 9
<211> LENGTH: 118
<212> TYPE: PRT
<213> ORGANISM: Hepatitis B virus

<400> SEQUENCE: 9

Met Gly Leu Ser Trp Thr Val Pro Leu Glu Trp Gly Lys Asn Leu Ser
1               5                   10                  15

Ala Ser Asn Pro Leu Gly Phe Leu Pro Asp His Gln Leu Asp Pro Ala
            20                  25                  30

Phe Arg Ala Asn Thr Asn Asn Pro Asp Trp Asp Phe Asn Pro Lys Lys
        35                  40                  45

Asp Pro Trp Pro Glu Ala Asn Lys Val Gly Val Gly Ala Tyr Gly Pro
    50                  55                  60

Gly Phe Thr Pro Pro His Gly Gly Leu Leu Gly Trp Ser Pro Gln Ser
65                  70                  75                  80

Gln Gly Thr Leu Thr Thr Leu Pro Ala Asp Pro Pro Pro Ala Ser Thr
                85                  90                  95

Asn Arg Gln Ser Gly Arg Gln Pro Thr Pro Ile Ser Pro Pro Leu Arg
            100                 105                 110

Asp Ser His Pro Gln Ala
        115

<210> SEQ ID NO 10
<211> LENGTH: 108
<212> TYPE: PRT
<213> ORGANISM: Hepatitis B virus

<400> SEQUENCE: 10

Met Gly Gln Asn His Ser Val Thr Asn Pro Leu Gly Phe Phe Pro Asp
1               5                   10                  15
```

His Gln Leu Asp Pro Leu Phe Arg Ala Asn Ser Asn Asn Pro Asp Trp
            20                  25                  30

Asp Phe Asn Pro Asn Lys Asp Thr Trp Pro Glu Ala Thr Lys Val Gly
        35                  40                  45

Val Gly Ala Phe Gly Pro Gly Phe Thr Pro Pro His Gly Gly Leu Leu
    50                  55                  60

Gly Trp Ser Pro Gln Ala Gln Gly Ile Leu Thr Thr Leu Pro Ala Ala
65                  70                  75                  80

Pro Pro Pro Ala Ser Thr Asn Arg Gln Ser Gly Arg Lys Ala Thr Pro
                85                  90                  95

Ile Ser Pro Pro Leu Arg Asp Thr His Pro Gln Ala
            100                 105

<210> SEQ ID NO 11
<211> LENGTH: 119
<212> TYPE: PRT
<213> ORGANISM: Hepatitis B virus

<400> SEQUENCE: 11

Met Gly Ala Pro Leu Ser Thr Ala Arg Arg Gly Met Gly Gln Asn Leu
1               5                   10                  15

Ser Val Pro Asn Pro Leu Gly Phe Phe Pro Asp His Gln Leu Asp Pro
            20                  25                  30

Leu Phe Arg Ala Asn Ser Ser Ser Pro Asp Trp Asp Phe Asn Thr Asn
        35                  40                  45

Lys Asp Asn Trp Pro Met Ala Asn Lys Val Gly Val Gly Gly Phe Gly
    50                  55                  60

Pro Gly Phe Thr Pro Pro His Gly Gly Leu Leu Gly Trp Ser Pro Gln
65                  70                  75                  80

Ala Gln Gly Ile Leu Thr Thr Ser Pro Pro Asp Pro Pro Pro Ala Ser
                85                  90                  95

Thr Asn Arg Arg Ser Gly Arg Lys Pro Thr Pro Val Ser Pro Pro Leu
            100                 105                 110

Arg Asp Thr His Pro Gln Ala
        115

<210> SEQ ID NO 12
<211> LENGTH: 108
<212> TYPE: PRT
<213> ORGANISM: Hepatitis B virus

<400> SEQUENCE: 12

Met Gly Gln Asn Leu Ser Val Ser Asn Pro Leu Gly Phe Phe Pro Glu
1               5                   10                  15

His Gln Leu Asp Pro Leu Phe Arg Ala Asn Thr Asn Asn Pro Asp Trp
            20                  25                  30

Asp Phe Asn Pro Asn Lys Asp Thr Trp Pro Glu Ala Thr Lys Val Gly
        35                  40                  45

Val Gly Ala Phe Gly Pro Gly Phe Thr Pro Pro His Gly Gly Leu Leu
    50                  55                  60

Gly Trp Ser Pro Gln Ala Gln Gly Val Thr Thr Ile Leu Pro Ala Val
65                  70                  75                  80

Pro Pro Pro Ala Ser Thr Asn Arg Gln Ser Gly Arg Gln Pro Thr Pro
                85                  90                  95

Ile Ser Pro Pro Leu Arg Asp Thr His Pro Gln Ala
            100                 105

```
<210> SEQ ID NO 13
<211> LENGTH: 105
<212> TYPE: PRT
<213> ORGANISM: Hepatitis B virus

<400> SEQUENCE: 13

Met Gly Leu Asn Gln Ser Thr Phe Pro Leu Gly Phe Phe Pro Ser His
1               5                   10                  15

Gln Leu Asp Pro Leu Phe Lys Ala Asn Ala Gly Ser Ala Asp Trp Asp
            20                  25                  30

Lys Pro Lys Asp Pro Trp Pro Gln Ala His Asp Thr Ala Val Gly Ala
        35                  40                  45

Phe Gly Pro Gly Leu Val Pro Pro His Gly Gly Leu Leu Gly Trp Ser
    50                  55                  60

Ser Gln Ala Gln Gly Leu Ser Val Thr Val Pro Asp Thr Pro Pro Pro
65                  70                  75                  80

Pro Ser Thr Asn Arg Asp Lys Gly Arg Lys Pro Thr Pro Ala Thr Pro
                85                  90                  95

Pro Leu Arg Asp Thr His Pro Gln Ala
            100                 105

<210> SEQ ID NO 14
<211> LENGTH: 59
<212> TYPE: PRT
<213> ORGANISM: Artificial Sequence
<220> FEATURE:
<223> OTHER INFORMATION: HBV preS consensus sequence (for amino acid
      positions (-11) to 48)

<400> SEQUENCE: 14

Met Gly Gly Trp Ser Ser Thr Pro Arg Lys Gly Met Gly Thr Asn Leu
1               5                   10                  15

Ser Val Pro Asn Pro Leu Gly Phe Phe Pro Asp His Gln Leu Asp Pro
            20                  25                  30

Ala Phe Arg Ala Asn Ser Asn Asn Pro Asp Trp Asp Phe Asn Pro Asn
        35                  40                  45

Lys Asp His Trp Pro Glu Ala Asn Lys Val Gly
    50                  55

<210> SEQ ID NO 15
<211> LENGTH: 5
<212> TYPE: PRT
<213> ORGANISM: Artificial Sequence
<220> FEATURE:
<223> OTHER INFORMATION: N-terminal sequence X of the peptide of the
      lipopeptide-based compound of the present invention
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid

<400> SEQUENCE: 15

Asn Xaa Ser Xaa Xaa
1               5

<210> SEQ ID NO 16
<211> LENGTH: 6
<212> TYPE: PRT
```

```
<213> ORGANISM: Artificial Sequence
<220> FEATURE:
<223> OTHER INFORMATION: C-terminal sequence Y of the peptide of the
      lipopeptide-based compound of the present invention
<220> FEATURE:
<221> NAME/KEY: misc_feature
<222> LOCATION: (1)..(1)
<223> OTHER INFORMATION: Xaa can be any naturally occurring amino acid

<400> SEQUENCE: 16

Xaa His Gln Leu Asp Pro
1               5

<210> SEQ ID NO 17
<211> LENGTH: 18
<212> TYPE: PRT
<213> ORGANISM: Artificial Sequence
<220> FEATURE:
<223> OTHER INFORMATION: peptide of the lipopeptide-based compound of
      the present invention
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 17

Asn Xaa Ser Xaa Xaa Asn Pro Leu Gly Phe Xaa Pro Xaa His Gln Leu
1               5                   10                  15

Asp Pro

<210> SEQ ID NO 18
<211> LENGTH: 47
<212> TYPE: PRT
<213> ORGANISM: Hepatitis B virus

<400> SEQUENCE: 18

Gly Thr Asn Leu Ser Val Pro Asn Pro Leu Gly Phe Phe Pro Asp His
1               5                   10                  15

Gln Leu Asp Pro Ala Phe Gly Ala Asn Ser Asn Asn Pro Asp Trp Asp
            20                  25                  30

Phe Asn Pro Asn Lys Asp His Trp Pro Glu Ala Asn Lys Val Gly
        35                  40                  45

<210> SEQ ID NO 19
<211> LENGTH: 47
<212> TYPE: PRT
<213> ORGANISM: Hepatitis B virus

<400> SEQUENCE: 19

Gly Gln Asn Leu Ser Thr Ser Asn Pro Leu Gly Phe Phe Pro Asp His
1               5                   10                  15

Gln Leu Asp Pro Ala Phe Arg Ala Asn Thr Ala Asn Pro Asp Trp Asp
            20                  25                  30

Phe Asn Pro Asn Lys Asp Thr Trp Pro Asp Ala Asn Lys Val Gly
        35                  40                  45
```

```
<210> SEQ ID NO 20
<211> LENGTH: 47
<212> TYPE: PRT
<213> ORGANISM: Artificial Sequence
<220> FEATURE:
<223> OTHER INFORMATION: amino acid positions 2 to 48 of the HBV preS
      consensus sequence

<400> SEQUENCE: 20

Gly Thr Asn Leu Ser Val Pro Asn Pro Leu Gly Phe Phe Pro Asp His
1               5                   10                  15

Gln Leu Asp Pro Ala Phe Arg Ala Asn Ser Asn Asn Pro Asp Trp Asp
            20                  25                  30

Phe Asn Pro Asn Lys Asp His Trp Pro Glu Ala Asn Lys Val Gly
        35                  40                  45

<210> SEQ ID NO 21
<211> LENGTH: 47
<212> TYPE: PRT
<213> ORGANISM: Artificial Sequence
<220> FEATURE:
<223> OTHER INFORMATION: Amino acid sequence of control peptide mutant
      MyrB Ala11-15

<400> SEQUENCE: 21

Gly Thr Asn Leu Ser Val Pro Asn Pro Ala Ala Ala Ala Ala Asp His
1               5                   10                  15

Gln Leu Asp Pro Ala Phe Gly Ala Asn Ser Asn Asn Pro Asp Trp Asp
            20                  25                  30

Phe Asn Pro Asn Lys Asp His Trp Pro Glu Ala Asn Lys Val Gly
        35                  40                  45

<210> SEQ ID NO 22
<211> LENGTH: 77
<212> TYPE: PRT
<213> ORGANISM: Artificial Sequence
<220> FEATURE:
<223> OTHER INFORMATION: Amino acid sequence of control peptide preS2-
      78myr

<400> SEQUENCE: 22

Gly Gln Asn Leu Ser Thr Ser Asn Pro Leu Gly Phe Phe Pro Asp His
1               5                   10                  15

Gln Leu Asp Pro Ala Phe Arg Ala Asn Thr Ala Asn Pro Asp Trp Asp
            20                  25                  30

Phe Asn Pro Asn Lys Asp Thr Trp Pro Asp Ala Asn Lys Val Gly Ala
        35                  40                  45

Gly Ala Phe Gly Leu Gly Phe Thr Pro Pro His Gly Gly Leu Leu Gly
    50                  55                  60

Trp Ser Pro Gln Ala Gln Gly Ile Leu Gln Thr Leu Pro
65                  70                  75
```